United States Patent [19]

Wong et al.

[11] Patent Number: 6,013,451
[45] Date of Patent: Jan. 11, 2000

[54] BACILLUS STEAROTHERMOPHILUS DNA POLYMERASE I (KLENOW) CLONES INCLUDING THOSE WITH REDUCED 3'- TO -5' EXONUCLEASE ACTIVITY

[75] Inventors: Victor Thi Wong Wong, Singapore; Seng Meng Phang, Singapore; Tien Chye Tan, Jalan Rabu, all of Singapore

[73] Assignee: The National University of Singapore, Singapore, Singapore

[21] Appl. No.: 09/057,969

[22] Filed: Apr. 3, 1998

[30] Foreign Application Priority Data

Apr. 10, 1997 [SA] Saudi Arabia ................ 9701158

[51] Int. Cl.[7] ................ C12Q 1/68; C12P 19/34; C07H 21/02; C07H 21/04
[52] U.S. Cl. ................ 435/6; 435/91.2; 435/194; 536/22.1; 536/23.1; 536/24.1; 536/24.31; 536/24.32; 536/24.33; 536/24.3
[58] Field of Search ................ 536/22.1, 23.1, 536/24.1, 24.3, 24.39, 24.23; 435/6, 91.2, 194

[56] References Cited

U.S. PATENT DOCUMENTS

| | | | |
|---|---|---|---|
| 5,716,819 | 2/1998 | Chatterjee | 435/194 |
| 5,747,298 | 5/1998 | Hong et al. | 435/91.1 |
| 5,814,506 | 9/1998 | Kong et al. | 435/194 |

FOREIGN PATENT DOCUMENTS

WO 95/27067  10/1995  WIPO .

OTHER PUBLICATIONS

Ito et al., 1992, Nucleic Acids Res., vol. 19, No. 15, pp. 4045–4057.
Bernad et al., 1987, EMBO J., vol. 6, pp. 4219–4225.
Derbyshire et al., 1993, Methods in Enzymology, vol. 262, pp. 363–385.
Uemori et al., 1993, J. Biochem., vol. 113, pp. 401–410.
Kaboev et al., 1981, Journal of Bacteriology, vol. 145, pp. 21–26.
Stenesh et al., 1972, Biochim. Biophys. Acta, vol. 272, pp. 156–166.
Phang et al., 1995, Gene, vol. 163, pp. 65–68.
Kiefer et al., 1998, Nature, vol. 391, pp. 304–307.
Kiefer et al., 1997, Structure, vol. 5, pp. 95–108.
Bernad et al., 1989, Cell, vol. 59, pp. 219–228.
Blanco et al., 1992, Gene, vol. 112, pp. 139–144.
Krantz, 1992, Gene, vol. 112, pp. 133–137.
Joyce, 1991, Current Opinion Struct. Biol., vol. 1, pp. 173–180.
McClary et al., 1991, DNA Sequencing and Mapping, vol. 1, pp. 173–180.
Mead et al., 1991, BioTechniques, vol. 11, pp. 76–86.
Aliotta et al., "Thermostable Bst DNA polymerase I lacks a 3'—5' proofreading exonuclease activity", Genetic Analysis: Biomolecular engineering 1:185–195 1996.
Chang et al., "The Exo–gap method employing the phage f1 endonuclease generated a nested set of unidirectional deletions", Gene 127:95–98 1993
Riggs et al., "Construction of single amino acid subtitution mutants of cloned Bacillus stearothermophilus DNA polymerase I which lack 5'—3'exonuclease activity", Biochimica et Biophysica Acta 1307:178–186 1996.

*Primary Examiner*—Jeffrey Fredman
*Attorney, Agent, or Firm*—Frommer Lawrence & Haug LLP; Thomas J. Kowalski

[57] ABSTRACT

Disclosed and claimed are isolated nucleic acid molecules encoding *Bacillus stearothermophilus* DNA polymerase (DNApolI), including the structural gene for DNApolI, such as DNApolI genes having insertions, deletions, inactivation, or mutations at the 5' end thereof and thus encode Bst polymerase I enzymes which lack or have reduced 3'–5' exonuclease activity, as well as methods for making and using such nucleic acid molecules and such polymerases. For instance, the nucleic acid molecules are useful for making the polymerases, for example, by expression of a vector comprising the nucleic acid molecules; and, the polymerases are useful in DNA sequencing and/or labelling. Thus, disclosed and claimed recombinant DNA clones corresponding to the *Bacillus stearothermophilus* DNA polymerase (DNApolI) structural gene with deletions at the 5' end. The polymerases from these recombinant DNA clones exhibit DNA synthesis domain activity but have reduced 3' to 5' exonuclease activity. Further, minor modifications at the 5' and 3' ends allow the clones to be manipulated by cloning and expressed as monomeric peptides. These deleted DNA clones give rise to truncated DNApolIK enzymes that are deficient in 3' to 5' exonuclease activity and are useful in nucleic acid synthesis by primer extension reactions, particularly DNA labelling and DNA sequencing reactions. Furthermore, these clones may be combined with other clones in heterologous constructs to create hybrid proteins.

50 Claims, 6 Drawing Sheets

FIG. 1

| FIG.1A | FIG.1B |
|---|---|
| FIG.1C | FIG.1D |

FIG. 1A

```
GCGTCGACAAGGGGCGCAGCCGCAACTCAGGCGGACGGCTGGCCCTTCGATCGTCAAGCACTTGGTGAG
GCGGTAGCCGCGCTTCTTTTTATGGCCCCCGCGTGTACAATAGAACAAGGAACGTCCGAGGAGGATGA

AACGATAAAGGGATTCATACGAACCAGTCTACGGGTTACGATGATGTTAAACAAAATTTGGCGAAGAGC
 N  D  K  G  I  H  T  N  A  V  Y  G  F  T  M  M  L  N  K  I  L  A  E  E

GGGGGCAGCAGACGCCGCCGAACTGTCGGAACAGTTCCGCTGTGCGCGAATTGTCAAAGCGTACCGCA
 G  R  Q  Q  T  P  P  E  L  S  E  Q  F  F  P  L  V  R  E  L  L  K  A  Y  R

TTTGCAGTGAAAGTCATTTCGGGCGACCGTGACTTAACCCAGCTGCTCCCGCAAGTGACGGTGAGATTA
 F  A  V  K  V  I  S  G  D  R  D  L  T  Q  L  A  S  P  Q  V  T  V  E  I

ATTGTCGACTTGAAAGGATTGATGGCGACAATCCGACAAATCCCTGGCGTGCCCGGCATCGGGAAAAAA
 I  V  D  L  K  G  L  M  G  D  K  S  D  N  I  P  G  V  P  G  I  G  K  K

CTGAAAGAAAATTTGCGCCAATACCGGGATCTGGCGCTTTTAAGCAAACAGCTGGCCGCTATTTGCCGACG
 L  K  E  N  L  R  Q  Y  R  D  L  A  L  L  S  K  Q  L  A  A  I  C  R  D
                                                   PK

CTCGGATTCCAGTGTGTTTCTCGACAAGATGCCGTCCAAACGATGAAGGCGAAAAGCCGCTGCCGGATGG
 L  G  F  Q  S  F  L  D  K  M  A  V  Q  T  D  E  G  E  K  P  L  A  G  M

AACTATCACCATGCCCGATTGTCGGAAAGGAATCGAACTGCTGGCGTGGCGTGTTGTTCGATCTGTTGCCG
 N  Y  H  H  A  P  I  V  G  I  A  L  A  N  E  R  G  R  F  F  L  R  P  E

GCGGCCGTGGCGCTAAATGGCAAGGAATCGAACTGCTGGCGTGGCGTGTTGTTCGATCTGTTGCTGGCCG
 A  A  V  A  L  N  G  K  G  I  E  L  A  G  V  G  V  V  F  D  L  L  L  A
```

FIG. 1B

```
GCGCATGCGGCTACATTACGGTGACGAGCGAAGTCGGGCGCGCACCGAGTTTACGATTCATTCCGAAGCCGGA      150

TGTTGAAAAACAGCTCGTCTTAATTGACGGCAACAGCGTGGCCGTACGCGCCTTTTTGCGCTTTTGCAT           300
 M  L  K  N  K  L  V  L  I  D  G  N  S  V  R  Y  R  A  F  F  A  L  P  L  L  H    26

AGCCGACCCACATTCTCGTTGCCGTTTGAGCGGGAAACGAGGTTCCGCCATGAAGTTCCAAGACTATAAAGGC        450
 Q  P  T  H  I  L  V  A  F  D  A  G  K  T  T  F  R  H  E  T  F  Q  D  Y  K  G    76

TCCCCGCCTATGAGCTCGACCATTATGAAGCGGATGACATCATCGGAACGATGGCGGCGCGTGAGCGAGAAGGG      600
 I  P  A  Y  E  L  D  H  Y  E  A  D  D  I  I  G  T  M  A  A  R  E  R  E  G      126

CGAAAAAGGGATTACGACATCGAGTCGTACACGCCGGAGACGGTCGTGGAAAATACGGCCTCACCCGGAGCAA        750
 T  K  K  G  I  T  D  I  E  S  Y  T  P  E  T  V  V  E  K  Y  G  L  T  P  E  Q   176

CAGCGGTCAAGCTGCTCAAGCAATTCGGCACGGTCGAAAACGTACTGGCATCGATAGATGAGATCAAGGGAGAAG     900
 T  A  V  K  L  L  K  Q  F  G  T  V  E  N  V  L  A  S  I  D  E  I  K  G  E  K   226

CCCCGGTTGAGCTGACGCTCGATGACATTGTCTACAAGGAGAAGACCGGAAAAGTGGTGCCCTGTGTTCAGGAG      1050
 A  P  V  E  L  T  L  D  D  I  V  Y  K  G  E  D  R  E  K  V  V  A  L  F  Q  E   276

ATTTTGGATGCCGACAGCGTCACGGACGAAATGCTCGCCGACAAAGCGGCGCTGGTGGTGGAGGTGGTGGGCGAC     1200
 D  F  I  A  D  S  V  T  D  E  M  L  A  D  K  A  A  L  V  V  E  V  V  G  D      326
                                                                    PI

CGGCCGTCGCCGATCCGAAATTTCTCGCTTGGCTTGGCGATGAGACGAAGAAGAAAACGATGTTTGATTCAAAGCGG   1350
 T  A  V  A  D  P  K  F  L  A  W  L  G  D  E  T  K  K  K  T  M  F  D  S  K  R   376

CTTACTTGCTCGATCCGGCAGCGGCGGCGGCCAGCGGGGACGTTGCCGGTGGCGAAATCATCAGTACGAGGCGGTGCGA  1500
 A  Y  L  L  D  P  A  Q  Q  A  A  G  D  V  A  A  V  A  K  M  H  Q  Y  E  A  V  R   426
```

FIG. 1C

```
TCGGATGAGGCGGTCTATGGAAAAGGAGGAAGCGAAGGACGGTTCCTGATGAACCGACGCTGCCGAGCAGCTCG
 S  D  E  A  V  Y  G  K  G  G  K  R  T  V  P  D  E  P  T  L  A  E  Q  L

CTGACCGAGCTCGAACACGCGCTGGCCATTTGGCCAATATGGAATTTACTGGAGTGAAAGTGGACACGA
 L  T  E  L  E  H  A  L  A  G  I  L  A  N  M  E  F  T  G  V  K  V  D  T

CAAGAGTTCAACATTAACTCGCCGAAACAGCTCGGACGGTTTTATTTGACAAGCTCCCGGTGTTGA
 Q  E  F  N  I  N  S  P  K  Q  L  G  T  V  L  F  D  K  L  Q  L  P  V  L
                    P3

ATTTTGCATTACGCCAACTCGGCAAGCTGCAGTCAACGTATATTGAAGGGCTGCTGAAAGTGGTGCACCCG
 I  L  H  Y  R  Q  L  G  K  L  Q  S  T  Y  I  E  G  L  L  K  V  V  H  P

CAAAACATTCCGATTCGGCTTGAGGAAGGCGAAAATCCGCAAGCTGTCGTGCCGAGCCCGGACTGCC
 Q  N  I  P  I  R  L  E  E  G  R  K  I  R  Q  A  F  V  P  S  E  P  D  W

GCGTTCCGGCGCTGTTGGACATCCATACGAAAACAGCCATGGACATTTTCCATGTGACGGAAGAAGACGTGA
 A  F  R  R  W  L  D  I  H  T  K  T  A  M  D  I  F  H  V  S  E  E  D  V

AACTTGAACATTACGCGCAAAGAAGCGGCTGAATTTATTGAGCGATATTTGCCAGTTTTCCAGTGTAAAGC
 N  L  N  I  T  R  K  E  A  A  E  F  I  E  R  Y  F  A  S  F  P  G  V  K

CCCGATATTACAAGCCCGCAACTTCAACGTCCGCAGTTCGCCGAGCGAGCGCGATGAACACCGATCCAGG
 P  D  I  T  S  R  N  F  N  V  R  T  F  A  E  R  T  A  M  N  T  P  I  Q

CTGTTGCTGCAAGTCATGACGAACTCATTTTGGAGGCGCCGAAAGAGAAATCGAACGGCTGCCGCTG
 L  L  L  Q  G  H  D  E  L  I  L  E  A  P  K  E  E  I  G  R  L  C  R  L

CGGCCAAATAAAGCGCCTGCCCGCAGCTGCTCCGGTTTTCACGGGCCGACGACAATGAGCTGTGCTTT
 A  K  *
```

FIG. 1D

```
     P2
TCCGCAAGGCGGCGCCATTTGGGCGCTTGAAGAGCCGTTGATGGACGAACTGCCGCAACGAACAAGATGGCTG    1650
 V  R  K  A  A  I  W  A  L  E  E  P  L  M  D  E  L  R  R  N  E  Q  D  R  L    476

AGCGGCTTGAACAGATGGGCGCGGAGCTCACCGAGCAGCTGCAGGCGGTTGAGCGGGCATTTACGAACTCGCCGC    1800
 K  R  L  E  Q  M  G  A  E  L  T  E  Q  L  Q  A  V  E  R  R  I  Y  E  L  A  G    526

AAAAGACAAAAACCGGCTATTCAGCGATGTCAGCCGATGTCTAGAAAAGCTTGCACCGACTGAAATGTCGAACAT    1950
 K  K  T  K  T  G  Y  S  T  S  A  D  V  L  E  K  L  A  P  H  H  E  I  V  E  H    576

TGACGGGCAAAGTGCACACGATGTTCAATCAGGGCGTTGACGCAAACCGGCCTCAGCTCCGTCGAACCGAATTTG    2100
 V  T  G  K  V  H  T  M  F  N  Q  A  L  T  Q  T  G  R  L  S  S  V  E  P  N  L    626
                                          P4

TCATCTTTGCGGCCGATTATTCGCAAATCGAGCTGCGTGTCCTCGCCATATGCGAAGATGACAATTGATTGAA    2250
 L  I  F  A  A  D  Y  S  Q  I  E  L  R  V  L  A  H  I  A  E  D  D  N  L  I  E    676

CAGCCAACATGCGCCGCCAAGGCCGTCAATTTTGGCATCGTGTACGGCATTAGTGATTACGGTCTCGGCGCAA    2400
 T  A  N  M  R  R  Q  A  K  A  V  N  F  G  I  V  Y  G  I  S  D  Y  G  L  A  Q    726

AATATATGGACAACATTGTGCAAGAAGCGAAACAAAAAGGGTATGTGACGACGCTGCTGCATCGGCGCCGCTATTTG    2520
 Q  Y  M  D  N  I  V  Q  E  A  K  Q  K  G  Y  V  T  T  L  L  H  R  R  R  Y  L    776

GATCCGCTGCCGACATCATTAAGAAGCGATGATCTAAGCGTTGAGCGTTGCGAAGAACGGCTGCAGGCGCGC    270
 G  S  A  A  D  I  I  K  K  A  M  I  D  L  S  V  S  V  R  E  E  R  L  Q  A  R    826

TTCCGGAAGTGATGGAGCAGGCAAGCCGTGACACTTCGCGTGCCGCTGAAAGTCGATTACCATTACGGTCCGACGTGGTAC    2850
 V  P  E  V  M  E  Q  A  V  T  L  R  V  P  L  K  V  D  Y  H  Y  G  P  T  W  Y    876

AAAACAGGTGCACGAACAGGAAAAGGAGGAGGC 3'
```

BACILLUS STEAROTHERMOPHILUS DNA POLYMERASE I (KLENOW) CLONES INCLUDING THOSE WITH REDUCED 3'- TO -5' EXONUCLEASE ACTIVITY

CROSS REFERENCE TO RELATED APPLICATIONS

This application claims priority from Singapore Application No. 9701158-9, filed Apr. 10, 1997, incorporated herein by reference.

FIELD OF THE INVENTION

The present invention relates: to a genomic clone of *Bacillus stearothermophilus*, such as a gene or isolated nucleic acid molecule encoding a DNA polymerase from *Bacillus stearothermophilus*; to Klenow-like fragments therefrom; to expression products thereof; to uses thereof, e.g., in manual or automated DNA sequencing and/or labeling; to isolated nucleic acid molecules or genes from *Bacillus stearothermophilus*, e.g., from the *Bacillus stearothermophilus* ("Bst") DNA polymerase (DNApolI) gene, having deletions therein, e.g., from the 5' end; to expression products thereof, e.g., which are 3' to 5' exonuclease-deficient or which have reduced 3' to 5' activity; and to uses thereof, e.g., in manual or automated DNA sequencing and/or labeling.

Thus, the invention also pertains to Bst DNA polymerases which have reduced 3' to 5' exonuclease activity or which are deficient in 3' to 5' exonuclease activity, as well as to uses thereof in manual or automated DNA sequencing and/or labeling; and, the invention pertains to isolated nucleic acid molecules encoding Bst polymerases having reduced 3' to 5' activity (e.g., portions of the Bst DNApolI gene).

The isolated nucleic acid molecules or genes from Bst DNApolI which are truncated at the 5' end (in comparison to full length Bst DNApolI) are also herein called "deleted clones" and give rise to truncated *B. stearothermophilus* DNA polymerase (DNApolI) enzymes that are deficient in 3' to 5' exonuclease activity or have reduced 3' to 5' exonuclease activity and are thus useful in nucleic acid synthesis by primer extension reactions, particularly DNA sequencing and DNA labelling reactions. These deleted clones may be combined with other isolated nucleic acid molecules, e.g., other deleted clones, to create hybrid proteins with novel properties.

Accordingly, the invention also relates to vectors containing and/or expressing the isolated nucleic acid molecules, and to methods for expressing the isolated nucleic acid molecules, including isolating the polymerase products from such expression; and, to methods for sequencing or labeling DNA including such polymerase products.

Several documents are cited in the following text, with either full citation where the document is cited, or with full citation appearing in a Document List prior to the claims. These documents relate to the state of the art to which this invention pertains, and each and every document cited in the following text, as well as all documents cited in each and every document cited in the following text, are hereby incorporated herein by reference.

BACKGROUND OF THE INVENTION

DNA polymerases synthesize DNA molecules in the 5' to 3' direction from deoxynucleoside triphosphates (nucleotides) using a complementary template DNA strand and a primer by successively adding nucleotides to the free 3'-hydroxyl group of the growing strand. The template strand determines the order of addition of nucleotides via Watson-Crick base pairing. In cells, DNA polymerases are involved in DNA repair synthesis and replication (Kornberg, 1974, In DNA Synthesis. W. H. Freeman, San Francisco).

*Escherichia coli* DNA polymerase I (DNApolI) and other homologous polymerases have three enzymatic functions: i) a 5' to 3' exonuclease activity, ii) a 3' to 5' exonuclease activity and iii) a DNA synthesis activity. The latter two functions are located towards the COOH-end of the protein, within a 'Klenow' fragment (DNApolIK). Enzyme preparations of *E. coli* DNA pol I can be treated with subtilisin to yield a *E. coli* DNApolIK minus the 5' to 3' exonuclease activity (see Brown et al., 1982, J Biol. Chem. 257: 1965–1972; Joyce et al., 1982, J. Biol. Chem. 257: 1958–1964; Joyce et al., 1983, Proc Natl Acad Sci USA 80: 1830–1834; Klenow & Henningsen, 1970, Proc. Natl. Acad. Sci. USA 65: 168–175; Kornberg, 1974; Setlow, P. et al., 1972, J. Biol. Chem. 247: 224–231; Setlow and Kornberg, 1972, J. Biol. Chem. 247: 232–240; Steitz and Joyce, 1987, In Protein Engineering, Chap. 20, pp. 227–235. Oxender, D. A., and Fox, C. F. (eds). Alan R. Liss, New York). It has been shown that the DNApolI gene is unstable, although the DNApolIk gene has been cloned and is stable (Joyce et al., 1982, J. Biol. Chem. 257: 1958–64; Joyce et al., 1983, PNAS USA 80: 1830–34).

Research on *E. coli* DNApolIK has indicated that the sites of the 3' to 5' exonuclease and DNA synthesis activities may be separated as their corresponding substrates do not compete. The DNA synthesis active site binds to double-stranded DNA containing a single-stranded 5' extension and deoxynucleoside triphosphate (dNTP) whereas the 3' to 5' exonuclease active site binds to deoxynucleoside monophosphate (dNMP) (Ollis et al., 1985, Nature 313: 762–766). The existence of a conserved 3' to 5' exonuclease active site present in a number of DNA polymerases was predicted by Bernat et al., 1989, Cell 59: 219–228; Blanco et al., 1992, Gene 112: 139–144; Reha-Krantz, L. J., 1992, Gene 112: 133–137.

Crystal structure analysis of *E. coli* DNApolIK has shown that its peptide chain is folded into two distinct domains, with the smaller domain of 200 amino acid residues being the 3' to 5' exonuclease domain and the other domain of 400 amino acid residues being the DNA synthesis domain (Ollis, 1985).

Evidence using modified DNA substrates further supports the hypothesis that the 3' to 5' exonuclease domain is separate from the DNA synthesis domain (Cowart et al., 1988, Biochem. 20: 1973–1983). This view is also supported by base mutations and deletions in related T4 and T5 DNA polymerases (Frey et al., 1992, Proc. Natl. Acad. Sci. USA 90: 2579–2583; Leavitt et al., 1989, Proc. Natl. Acad. Sci USA 86: 4465–4469; Spacciapoli, P. and Nossal, N. G., 1994, J. Biol. Chem. 269: 438–446).

Both the 3' to 5' exonuclease and the DNA synthesis domains of *E. coli* DNA polymerase I have been cloned, expressed, and characterized independently. The 3' to 5' exonuclease domain consists of approximately 200 amino acids. The DNA synthesis domain contains approximately 400 amino acids. There is, however, 50-fold less activity in the DNA synthesis domain when compared to the *E. coli* DNApolIK (Morrison et al., 1991, Proc. Natl. Acad Sci. USA, 88: 9473–9477).

*Bacillus stearothermophilus* is a mesophilic bacterium. The DNApolI of *Bacillus stearothermophilus* displays optimum activity at 67° C. Its amino acid sequence shows a high level of homology to that of *E. coli* polI. Other similarities include the presence of three active domains: 5' to 3' exonuclease, 3' to 5' exonuclease, and DNA synthesis (Kaboev et al., 1981, J. Bacteriol. 145: 21–26; Phang et al., 1995, Gene 163: 65–68; Stenesh and Roe, 1972, Biochim. Biophys. Acta 272: 156–166; Ye and Hong, 1987, Scientia Sinica 30: 503–506). Limited proteolysis with subtilisin also results in a small fragment with the 5' to 3' exonuclease activity and a large Klenow-like fragment (Lu et al., 1991, BioTechniques 11: 465–166; McClary et al., 1991, DNA Sequence 1: 173–180; Phange et al., 1995). The *B. stearothermophilus* DNApolI large Klenow-like fragement has been proposed to contain a domainc for the 3' to 5' exonuclease activity (Ye & Hong, 1987).

Many molecular cloning techniques and protocols involve the systhesis of DNA in in vitro reactions catalyzed by DNA polymerases. For example, DNA polymerases are used in DNA labelling and DNA sequencing reactions, using either 35S-, 32P- or 33P-labelled nucloetides. Most of these enzymes require a template and primer, and synthesize a product whose sequence is complementary to that of the template. The 5' to 3' exonuclease activity of *E. coli* DNA polymerases I is often troublesome in these reactions because it degrades the 5' terminus of primers that are bound to the DNA templates and removes 5' phosphates from the termini of DNA fragments that are to be used as substrates for ligation. The use of DNA polymerase for these labelling and sequencing reactions thus depends upon the removal of the 5' to 3' exonuclease activity.

The 5' to 3' exonuclease activity can be removed proteolytically from the holoenzyme without affecting either the polymerase activity of the 3' to 5' exonuclease activity. The klenow fragment of *E. coli* DNA polymerase I that is available. today from commercial sources consists of a single polypeptide chain produced by cleavage of intact DNA polymerase I with subtilisin or by cloning. This creates a DNApolIK containing only the 3' to 5' exonuclease and DNA synthesis activities (without the 5' to 3' exonuclease activity) and allows for net DNA processivity.

DNA processivity is performed by heat denaturation of a DNA template containing the target sequence, annealing of a primer to the DNA strand and extension of the annealed primer with a DNA polymerase. At low temperatures of about 37° C., the DNA may be insufficiently denatured and secondary structures may impede DNA processivity. This results in stoppage of primer extension (insufficient labelling in DNA labelling) or errors (e.g., band compression or cross-banding artifacts in DNA sequencing). Band compression is artifacts seen on sequencing gels when there is a run of G-C rich regions. This may be overcome by adding deaza- or inosine-nucleotides to substitute for guanosine nucleotides or preferably by performing DNA processivity at elevated temperatures. Cross-banding artifacts are caused by premature termination, mismatches, or both.

The incorporation of a thermostable subtilisin-treated DNA polymerase, such as that from *Bacillus stearothermophilus* DNApolI, into DNA sequencing reactions allows for these secondary structure artifacts to be overcome. *B. stearothermophilus* DNApolI has a temperature optimum of 67° C. and exhibits an ideal banding pattern with minimal or no crossbanding, due to the presence of a 3' to 5' exonuclease activity present in the enzyme. Crossbanding produces unreadable sequencing gels.

The subtilisin-digested *B. stearothermophilus* DNA polymerase I (DNApolI) is distinguished from other DNA polymerases by its high degree of DNA processivity and fidelity (Lu et al., 1991, BioTechniques 11: 465–466; McClary et al., 1991, DNA Sequence 1: 173–180; Mead et al., 1991, Biotechniques 11: 76–87; Ye & Hong, 1987, Sci. Sin. 30: 503–506). This is exemplified by readable DNA sequences on X-ray films of at least 350 bases with little or no cross-banding. In contrast, other DNA polymerases may have high degree of processivity but with poor fidelity, resulting in errors or cross-banding artifacts.

The high degree of polymerase activity is due to the DNA synthesis domain. The high fidelity conferred upon *B. stearothermophilus* DNApolI may be due to its proposed 3'–5' exonuclease activity (proofreading or editing function), which is proposed to reside independently of the DNA synthesis activity in a similar fashion to other Type I DNA polymerases as mentioned earlier; but Bst DNApolI may lack functional 3'–5' exonuclease activity (see Stellmann et al, infra).

Alternatively, high fidelity may not be due to the 3'–5' exonuclease activity, but rather, may be an inherent property of the DNA synthesis domain *B. stearothermophilus*; e.g., tighter binding of the enzyme to the DNA template may confer higher fidelity by preventing mismatches from occurring.

The concept of net DNA processivity, however, is the ratio of DNA synthesis activity versus 3'–5' exonuclease activity. DNA synthesis enzyme (synthetase) acts to polymerize nucleotides while 3'–5' exonuclease has an editing or proof-reading function. Thus high DNA synthesis is generally achieved at the expense of high fidelity and vice versa. The 3'-to-5' exonuclease activity of many DNA polymerases may, therefore, be disadvantageous in situations where one is trying to achieve net synthesis of DNA.

No document discussing DNA polymerase from *B. stearothermophilus* relates to a DNA polymerase enzme which exhibits reduced 3' to 5' exonuclease activity and which can give superior results in DNA amplification techinques and primer extention reactions. Further, prior documents do not appear to fully appreciate a genomic clone of *Bacillus stearothermophilus*, such as a gene or isolated nucleic acid molecule encoding a DNA polymerase from *Bacillus stearothermophilus*; Klenow-like fragments from expression thereof; or uses thereof, e.g., in manual or automated DNA sequencing and/or labeling.

There is thus a need for a *B. stearothermophilus* DNA polymerase I enzyme that has reduced 3' to 5' exonuclease activity or which is deficient in 3' to 5' exonuclease activity and can participate in various DNA amplifications schemes, including DNA sequencing and labelling, manual or automated. There is further a need for uses of the genomic clone of Bst, e.g., uses for nucleic acid molecules which encode a DNA polymerase from Bst, as well as for Klenow-like fragments therefrom and expression thereof; for example there is a need for producing DNA polymerases from Bst, and a need in manual or automated DNA sequencing and/or labeling for such polymerases.

OBJECTS AND SUMMARY OF THE INVENTION

This invention provides for *B. stearothermophilus* DNApolI derivatives with reduced 3'–5' exonuclease activity or which are deficient in 3' to 5' exonuclease activity. The present invention further provides nucleic acid molecules encoding such Bst DNApolI derivatives.

This invention also provides modular DNA polymerases with defined enzymatic domains which can be used in any combinations to create hybrid proteins with novel properties.

The present invention also provides a genomic clone of Bst which is useful for providing nucleic acid molecules which encode a DNA polymerase from Bst, as well as for providing Klenow-like fragments therefrom and expression products thereof. For example, this invention provides a means for producing DNA polymerases from Bst, and manual or automated DNA sequencing and/or labeling using such polymerases.

Accordingly, the invention has many objectives, which can include one or more of:

Providing nucleic acid molecules which encode a DNA polymerase from Bst, such as a nucleic acid molecule which with reference to full length Bst DNApolI has deletions therein, e.g., from the 5' end; a vector such as a recombinant containing the nucleic acid molecule, e.g., a recombinant containing and/or expressing a nucleic acid molecule encoding a *Bacillus stearothermophilus* DNA polymerase I such as a truncated *Bacillus stearothermophilus* DNA polymerase I (from expression of a Bst DNApolI nucleic acid molecule having deletions therein, e.g., from the 5' end), for instance a Bst DNA polymerase I which is deficient in or has reduced 3' to 5' exonuclease activity;

Providing *B. stearothermophilus* DNApolI derivatives (Klenow clones) with increasing deletions from the 5' end exhibiting reduced 3' to 5' exonuclease activity or lacking 3' to 5' exonuclease activity; and Providing *B. stearothermophilus* DNA polymerase I Klenow-like fragments with reduced 3' to 5' exonuclease activity or which are deficient in 3' to 5' exonuclease activity, that can participate in various DNA amplification schemes including DNA sequencing and DNA labelling reactions.

The use of the expression products of DNApolI clones or of DNApolI clones (including expression products from trucated or deleted versions of DNApolI or truncated or deleted versions of DNApolI clones) in manual or automated DNA sequencing and labelling techniques, e.g., providing methods for DNA sequencing or labelling including a Bst DNA polymerase from expression of an isolated nucleic acid molecule coding therefor, such as a Bst polymerase having reduced 3' to 5' exonuclease activity or which is deficient in such activity from expression of a truncated or deleted DNApolI.

Providing combined *B. stearothermophilus* DNApolI genes or portions thereof so as to express tandem or chimeric Bst polymerases with reduced 3' to 5' exonuclease activity or which are deficient in 3' to 5' exonuclease activity or providing Bst DNApol genes or portions thereof combined with DNA encoding other modular catalytic domains which upon expression yields tandem or chimeric novel proteins.

Accordingly, this present invention provides nucleic acid molecules encoding *B. stearothermophilus* DNA polymerase I enzymes and Klenow-like fragments therefrom and Bst DNA polymerase I enzymes from expression thereof, such as Bst DNA polymerase I enzymes having improved DNA processivity by removal of some or all of the 3' to 5' exonuclease activity of the enzyme, e.g, by deleting portions of the 5' end of the DNA polymerase gene (DNApolI). The present invention also provides methods for making such expression products or Klenow-like fragments, e.g., by inserting the nucleic acid molecules into a vector and isolating the expression products thereof; and, for using such expression products or Klenow-like fragments, e.g., in DNA sequencing or labelling.

The recombinant *B. stearothermophilus* DNA polymerase I enzymes, especially those with reduced 3' to 5' exonuclease activity, are not only useful in DNA synthesis and labelling reactions, but have wider applications in nucleotide amplification schemes; for instance, they can be used with nucleotides or their analogs which otherwise would not be incorporated because of the editing 3' to 5' exonuclease activity. Furthermore, these enzymes can be used in automated sequencing and labelling reactions.

The present invention, in certain particular embodiments, provides a series of *B. stearothermophilus* DNApolI structural genes of 1781 (PK), 1526 (P1), 1281 (P2), 1043 (P3) and 791 (P4) bp respectively, derived from the *B. stearothermophilus* DNApolI gene but with increasing deletions at the 5' end (deleted clones of *B. stearothermophilus* DNApolI) (2859 bp for genomic clone minus 1077, 1332, 1577, 1815 and 2067 bp, respectively; start positions re: FIG. 1 are plus one (1) bp, i.e., at 1078, 1333, 1578, 1816, and 2068, respectively). These genes encode Bst DNA polymerase enzymes which are 3' to 5' exonuclease-deficient or which have reduced 3' to 5' exonuclease activity or which may lack 3' to 5' exonuclease function. One can also obtain these Bst DNA polymerase enzymes which are 3' to 5' exonuclease-deficient or which have reduced 3' to 5' exonuclease activity by insertional inactivation or other means for interrupting expression of the full length Bst DNApolI gene such that the product ultimately expressed is the same as or homologous to the product from the bp 1781 (PK), 1526 (P1), 1281 (P2), 1043 (P3) and 791 (P4) Bst genes. Accordingly, one can use 5' end deletions, or interruptions such as insertional inactivation, to cause expression of pieces of DNApolI, such as the 1781 (PK), 1526 (P1), 1281 (P2), 1043 (P3) and 791 (P4) bp portions of DNApolI, to thereby obtain Bst DNA polymerase enzymes which are 3' to 5' exonuclease-deficient or which have reduced 3' to 5' exonuclease activity, or which may lack 3' to 5' exonuclease function. The Klenow fragment (Bst polIK; 593 aa starting at aa position 286, encoded by 1781 bp fragment starting at position 1078) is proposed to contain the 3' to 5' exonuclease and DNA synthesis domains but may lack 3' to 5' exonuclease function (Stellmann et al., J. Bacteriol. 1992, 174: 4350–55).

Thus, the deleted clones give rise to a series of four truncated *B. stearothermophilus* DNA polymerase I enzymes that are deficient in 3'–5' exonuclease activity or have reduced 3'–5' exonuclease activity and are useful in nucleic acid synthesis by primer extension reactions, particularly DNA cycle-sequencing reactions. Furthermore, deleted clones may be combined with each other to give novel enzymes, or with other nucleic acid molecules encoding catalytic domains, to give rise to chimeric enzymes with novel properties.

Thus, the present invention contemplates recombinant thermostable *B. stearothermophilus* DNA polymerase I enzymes with DNA synthesis activity but deficient in 3' to 5' exonuclease activity or having reduced 3' to 5' exonuclease activity. Preferably, the polymerase enzymes have an amino acid residue sequence represented by the formula shown in FIG. 1 (SEQ ID NOS: 1 and 2) from residue 371 (e.g., residues 1 to 370 are deleted), or from residue 453 (e.g., residues 1 to 452 are deleted), or from residue 532 (e.g., residues 1 to 531 are deleted), or from residue 616 (e.g., residues 1 to 615 are deleted). Additionally, the invention comprehends the Bst Klenow fragment which starts from residue 286 (e.g., residues 1 to 285 are deleted). The polymerases can culminate at residue 879.

Accordingly, the invention comprehends nucleic acid molecules encoding Bst polymerase I, such as DNA polymerase I having reduced or no or which may lack 3' to 5' exonuclease activity, e.g., nucleic acid molecules encoding polymerase enzymes have an amino acid residue sequence represented by the formula shown in FIG. 1 (SEQ ID NOS: 1 and 2) from residue 286 (e.g., residues 1 to 285 are deleted), or from residue 371 (e.g., residues 1 to 370 are deleted), or from residue 453 (e.g., residues 1 to 452 are deleted), or from residue 532 (e.g., residues 1 to 531 are deleted), or from residue 616 (e.g., residues 1 to 615 are deleted); for instance, an isolated nucleic acid molecule wherein nucleotides 1 to 1077 are deleted or interrupted, or an isolated nucleic acid molecule wherein nucleotides 1 to 1332 are deleted or interrupted, or an isolated nucleic acid molecule wherein nucleotides 1 to 1577 are deleted or interrupted, or an isolated nucleic acid molecule wherein nucleotides 1 to 1815 are deleted or interrupted, or an isolated nucleic acid molecule wherein nucleotides 1 to 2067 are deleted or interrupted; or wherein "reading" begins at nt 1078, 1333, 1578, 1816, or 2068.

This invention also provides to vectors such as plasmids containing a Bst gene, e.g., Bst DNApolI, or a functional portion of Bst DNApolI which encodes a 3' to 5' exonuclease deficient B. stearothermophilus DNA polymerase or a B. stearothermophilus DNA polymerase having reduced 3' to 5' exonuclease activity, and to cells, such as prokaryotic cells, transformed with a vector, such as a plasmid, of this invention.

Also, the invention comprehends modular DNA polymerases with defined enzymatic domains which can be combined to create hybrid proteins with novel properties.

These and other objects and embodiments are disclosed or are obvious from and encompassed by, the following Detailed Description.

BRIEF DESCRIPTION OF THE DRAWINGS

The following Detailed Description, given by way of example, but not intended to limit the invention to specific embodiments described, may be understood in conjunction with the accompanying Figures, incorporated herein by reference, in which:

FIG. 1 shows the nucleotide (SEQ ID NO: 1) and peptide (SEQ ID NO: 2) sequences of the B. stearothermophilus polymerase I (see Phang et al., 1992, Gene 163: 65–68; the methionine amino acid under the ATG start codon is in bold; the 5'-end primer sequences were designed to prime onto the underlined sequences and are labelled PK, P1, P2, P3 and P4 respectively; the 3'-end primer was the same for all clones and was based on a sequence located on the plasmid vector pTrc99A (see FIG. 2 and Example 3); and the NcoI internal site is indicated by a dotted line);

DETAILED DESCRIPTION

Definitions

Figure 2:
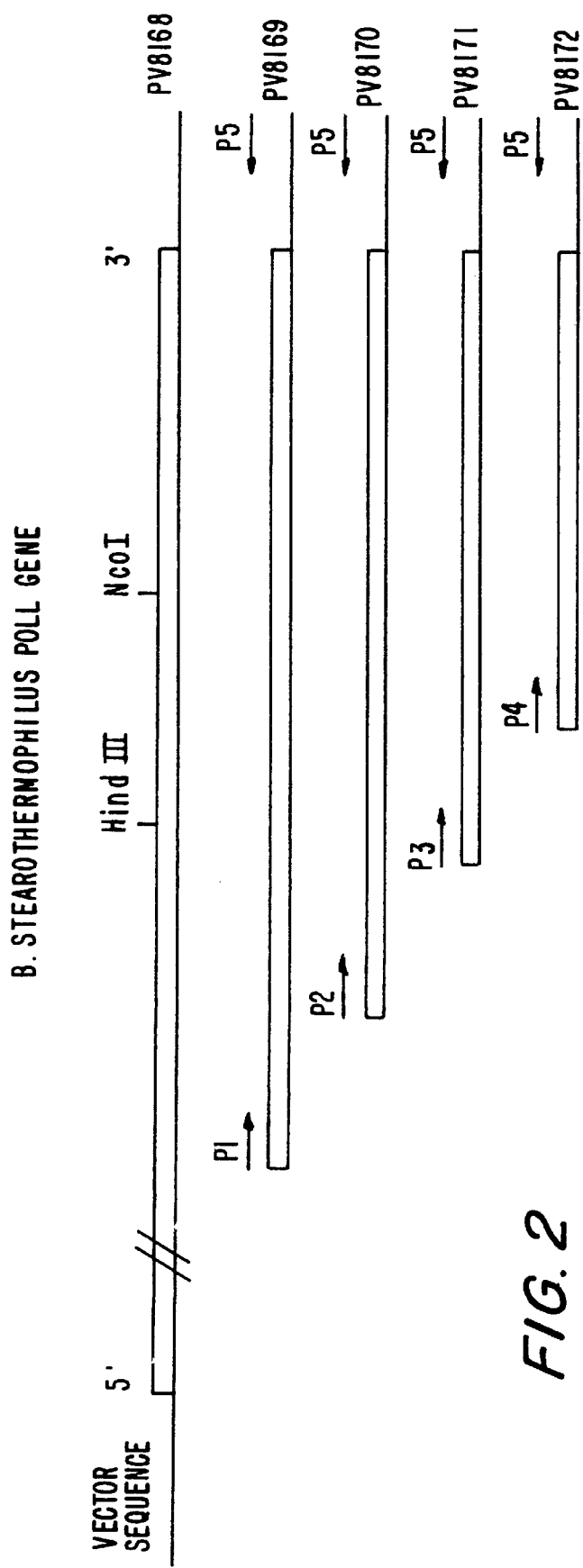
FIG. 2 shows a schematic diagram, not necessarily to scale, of deleted B. stearothermophilus DNApolI clones obtained by DNA amplification using specific 5' primers labelled PK, P1, P2, P3, P4 and a 3' primer labelled P5 (clones are labelled PV8168 (PK), PV8169, PV8170, PV8171, PV8172); and, FIG. 3 shows a schematic diagram of the cloning scheme employed to obtain the 5' deleted B. stearothermophilus DNApolI clones as described in the Examples.

The following terms are defined in order to provide a clear and consistent understanding of their use in the specification and the claims. Other terms are well known in the art so that they need not be defined herein.

Amino acid residues are numbered according to Phang et al., 1995, Gene 163: 65–68.

The "amino acid residues" described herein are preferred to be in the "L" isomeric form. However, residues in the "D" isomeric form can be substituted for any amino acid residue, as long as the desired functional property is retained by the polypeptide. $NH_2$ refers to the free amino group present at the amino terminus of a polypeptide. COOH refers to the free carboxy group present at the carboxy terminus of a polypeptide. The amino-terminal $NH_2$ group and carboxy-terminal COOH group of free polypeptides are typically not set forth in a formula. A hyphen at the amino- or carboxy-terminus of a sequence indicates the presence of a further sequence of amino acid residues or a respective $NH_2$ or COOH terminal group.

In keeping with standard polypeptide nomenclature, J. Biol. Chem., 243: 3552–3559 (1969) and adopted at 37 CFR §1.822(b)(2), abbreviations for amino acid residues are shown in the following Table of Correspondence:

| Table of Correspondence | | |
|---|---|---|
| | Symbol | Amino acid |
| Y | Tyr | tyrosine |
| G | Gly | glycine |
| F | Phe | phenylalanine |
| M | Met | methionine |
| A | Ala | alanine |
| S | Ser | serine |
| I | Ile | isoleucine |
| L | Leu | leucine |
| T | Thr | threonine |
| V | Val | valine |
| P | Pro | proline |
| K | Lys | lysine |
| H | His | histidine |
| Q | Gln | glutamine |
| E | Glu | glutamic acid |
| W | Trp | tryptophan |
| R | Arg | arginine |
| D | Asp | aspartic acid |
| N | Asn | asparagine |
| C | Cys | cysteine |

It should be noted that all amino acid residue sequences are represented herein by formulae whose left and right orientation is in the conventional direction of amino-terminus to carboxy-terminus.

An "analog" of a molecule such as B. stearothermophilus DNApolI is meant to refer to a molecule substantially similar in function to either the entire molecule or to a fragment thereof.

The term "base pair (bp)" relates to a partnership of adenine (A) with thymine (T), or of cytosine (C) with guanine (G) in a double-stranded DNA molecule.

As used herein, "cell", "cell line", and "cell culture" can be used interchangeably and all such designations include progeny. Thus, the words "transformants" or "transformed cells" include the primary subject cell and cultures derived therefrom without regard for the number of transfers. It is also understood that all progeny may not be precisely identical in DNA content, due to deliberate or inadvertent mutations. Mutant progeny that have the same functionality as screened for in the originally transformed cell are included.

As used herein, a molecule is said to be a "chemical derivative" of another molecule when it contains additional chemical moieties not normally a part of the molecule. Such moieties may improve the molecule's solubility, absorption, biological half life, etc.

"Clone" refers to any entity capable of replicating itself. As used herein, it refers to both the structural gene as well as to the replicated protein.

The term "control sequences" refers to DNA sequences necessary for the expression of an operably linked coding sequence in a particular host organism. The control sequences that are suitable for prokaryotes, for example, include a promoter, optionally an operator sequence, a ribosome binding site, and the like. Eukaryotic cells are known to utilize promoters, polyadenylation signals, and enhancers.

A "DNA polymerase substantially reduced in 3'–5' exonuclease activity" is defined herein as either (1) a mutated DNA polymerase that has about or less than the specific activity of the corresponding unmutated, wild-type enzyme, or (2) a DNA polymerase having a 3' to 5' exonuclease specific activity less than about 1 unit/mg protein, or preferably about or less than 0.1 units/mg protein. A unit of activity of 3' to 5' exonuclease is defined as the amount of activity that solubilizes 10 nmoles of substrate ends in 60 min. at 37° C., assayed as described in the "BRL 1989 Catalogue & Reference Guide", page 5, with HhaI fragments of lambda DNA 3'-end labeled with [3H]dTTP by terminal deoxynucleotidyl transferase (TdT). Protein concentration is measured by the method of Bradford, 1976, Anal. Biochem. 72: 248.

"Expression" is the process by which a promoter/structural gene produces a polypeptide. It involves transcription of the gene into messenger RNA (mRNA) and the translation of such mRNA into a polypeptide.

The term "expression system" refers to DNA sequences containing a desired coding sequence and control sequences in operable linkage, so that hosts transformed with these sequences are capable of producing the encoded proteins. In order to effect transformation, the expression system may be included on a vector; however, the relevant DNA may then also be integrated into the host chromosome.

"3' to 5' exonuclease activity" is an enzymatic activity well known to the art. This activity is often associated with DNA polymerases, and is thought to be involved in a DNA replication "editing" or correction mechanism.

A "fragment" of a molecule such as B. stearothermophilus DNApolI, is meant to refer to any polypeptide subset of the molecule.

A "functional derivative" of B. stearothermophilus DNApolI is a compound which possesses a biological activity (either functional or structural) that is substantially similar to a biological activity of B. stearothermophilus DNApolI. The term "functional derivative" is intended to include the "fragments" "variants," "analogues," or "chemical derivatives" of a molecule.

"Gene" is a DNA sequence that contains information necessary to express a polypeptide or protein. The term "gene" as used herein refers to a DNA sequence that encodes a polypeptide.

"Heterologous" refers to two DNA segments having different origins, i.e. not, in nature, being genetically or physically linked to each other. Heterologous also describes molecules that are in nature physically or genetically linked together but which are linked together in a substantially different way than is found in nature.

"Homology", as used herein, refers to the comparison of two different nucleic acid sequences. For the present purposes, assessment of homology is as a percentage of identical bases, not including gaps introduced into the sequence to achieve good alignment. Percent homology may be estimated by nucleic acid hybridization techniques, as well as by determining and comparing the exact base order of the two sequences.

"Host" is any prokaryotic or eukaryotic microorganism that is the recipient of a DNA molecule. The DNA molecule may contain, but is not limited to, a structural gene, a promoter and/or an origin of replication.

"Mutation" is any change that alters the DNA sequence. As used herein, a mutated sequence may have single or multiple changes that alter the nucleotide sequence of the DNA. Alterations of the DNA sequence include deletions (loss of one or more nucleotides in the DNA sequence) and/or substitutions (substituting a different nucleotide for the original nucleotide along the DNA sequence).

"Nucleotide" is a monomeric unit of DNA or RNA consisting of a sugar moiety (pentose), a phosphate, and a nitrogenous heterocyclic base. The base is linked to the sugar moiety via the glycosidic carbon (1' carbon of the pentose) and that combination of base and sugar is a nucleoside. When the nucleoside contains a phosphate group bonded to the 3' or 5' position of the pentose, it is referred to as a nucleotide. A sequence of operatively linked nucleotides is typically referred to herein as a "base sequence" or "nucleotide sequence", and is represented herein by a formula whose left to right orientation is in the conventional direction of 5' terminus to 3' terminus. Each nucleotide is characterized by its base. The four DNA bases are adenine (A), guanine (G), cytosine (C), and thymine (T). The four RNA bases are A, G, C and uracil (U).

The term "oligonucleotide" as used herein is defined as a molecule composed of two or more deoxyribonucleotides and/or ribonucleotides. Its exact size will depend on many factors, which in turn depend on the ultimate function or use of the oligonucleotide. The oligonucleotide may be derived synthetically or by cloning.

"Operably linked" refers to juxtaposition such that the normal function of the components can be performed. Thus, a coding sequence "operably linked" to control sequences refers to a configuration wherein the coding sequences can be expressed under the direction of the control sequences.

"Origin of replication" refers to a DNA sequence from which DNA replication is begun, thereby allowing the DNA molecules which contain said origin to be maintained in a host, i.e., replicate autonomously in a host cell.

The term "primer" as used herein refers to an oligonucleotide, whether occurring naturally or produced synthetically, which is capable of acting as a point of initiation of nucleic acid synthesis when placed under conditions in which synthesis of a primer extension product which is complementary to a nucleic acid strand is induced, i.e., in the presence of four different nucleotide triphosphates and a polymerase enzyme in an appropriate buffer.

The primer is preferably single-stranded for maximum efficiency in DNA amplification, but may alternatively be double-stranded. If double-stranded, the primer is first treated to separate its strands before being used to prepare extension products. Preferably, the primer is an oligodeoxyribonucleotide. The primer must be sufficiently long to prime the synthesis of extension products in the presence of a polymerase enzyme. The exact lengths of the primers will depend on many factors, including temperature, source of primer and use of the method. For example, depending on the complexity of the target sequence, the oligonucleotide primer typically contains 15–25 nucleotides although it may contain more or fewer nucleotides. Short primer molecules generally require colder temperatures to form sufficiently stable hybrid complexes with the template.

The primers herein are selected to be "substantially" complementary to the different strands of each specific sequence to be amplified. This means that the primers must be sufficiently complementary to hybridize with their respective strands. Therefore, the primer sequence need not reflect the exact sequence of the template. For example, a non-complementary nucleotide fragment may be attached to the 5' end of the primer, with the remainder of the primer sequence being complementary to the strand. Alternatively, non-complementary bases or longer sequences can be interspersed into the primer, provided that the primer sequence has sufficient complementarily with the sequence of the strand to be amplified to hybridize therewith and thereby form a template for synthesis of the extension product of the primer. However, for detection purposes, particularly using labeled sequence-specific probes, the primers typically have exact complementarily to obtain the best results.

Generally, the synthesis will be initiated at the 3' end of each primer and will proceed in the 5' direction along the template strand, until synthesis terminates, producing molecules of different lengths.

"Processive" is a term of art referring to an enzyme's property of acting to synthesize or hydrolyse a polymer without dissociating from the particular polymer molecule. For the purposes of the present invention, processive refers to enzymes that add, on the average, at least 100, and preferably, about 200 or more, nucleotides before dissociation.

"Promoter" is a term of art referring to sequences necessary for transcription. It does not include ribosome binding sites and other sequences primarily involved in translation.

"Purifying" refers to increasing the specific activity of an enzymatic activity over the level produced in a culture in terms of units of activity per weight of protein. This term does not imply that a protein is purified to homogeneity.

"Structural gene" is a DNA sequence that is transcribed into messenger RNA that is then translated into a sequence of amino acid residues characteristic of a specific polypeptide. A "structural gene" may contain a heterologous ribosome binding site, replacing its natural (homologous) ribosome binding site as well as additional sequences to allow its rapid cloning into suitable vectors.

"Substantially pure" means that the desired purified enzyme is essentially free from contaminating cellular components which are associated with the desired enzyme in nature. Contaminating cellular components may include, but are not limited to, phosphatases, exonucleases or endonucleases.

A molecule is said to be "substantially similar" to another molecule if both molecules have substantially similar structures or if both molecules possess a similar biological activity. Thus, provided that two molecules possess a similar activity, they are considered variants as that term is used herein even if the structure of one of the molecules is not found in the other, or if the sequence of amino acid residues is not identical.

A "variant" of a molecule such as *B. stearothermophilus* DNApolI is meant to refer to a molecule substantially similar in structure and function to either the entire molecule, or to a fragment thereof.

B Stearothermophilus DNA Pol I Genes, Including Truncated Versions

The *B. stearothermophilus* DNApolI gene has been cloned and sequenced (see Phang et al., 1995, Gene 163: 65–68). The nucleotide and amino acid sequences are provided in FIG. 1 and as SEQ ID NOS: 1 and 2, respectively. The recombinant enzyme exhibits similar DNA sequencing properties to the native (wild type) enzyme.

Various properties of the Bst polymerase enzyme have been studied. For example, Hong et al., EP 0 712 927 A2, is directed particularly to a Bst enzyme possessing 3' to 5' exonuclease activity.

Kong, EP 0757 100 A1, relates specifically to an isolated DNA molecule consisting of nucleotides 868 to 2631 of Kong's SEQ ID No: 1, as well as a substantially pure recombinant Bst DNA polymerase substantially free of 3' to 5 exonuclease activity expressed by that isolated DNA molecule. The Kong clone has only 80% homology to that of the polymerase clones of the present invention. Therefore, it is likely that Kong's clone is DNA polymerase III, not DNA polymerase I, as in the present invention.

Riggs et al, Biochimica et Biophysica Acta, 1307 (1996) 178–186 relates to a full-length Bst clone that appears to have 98% homology with that of Phang et al. (see Aliotta et al., Genetic Analysis: Biomolecular Engineering 12 (1996) 185–95). However, Riggs' clone is from a different Bst strain. Further, Riggs has a two (2) amino acid break within their Klenow-like fragment and approximately 28 additional amino acids at their $NH_2$-terminal end (with respect to the longest exemplified polymerase of the invention, namely Bst polIK, the Bst Klenow fragment which starts from aa 286, such that as to other exemplified polymerases Riggs has even more additional amino acids). More particularly, Riggs removed 5'–3' exonuclease activity by base mutations, while retaining the full-length sequence, and Riggs also removed 5'–3' exonuclease activity to create a specific deleted Klenow-like fragment.

In contrast, in the present invention 5'–3' exonuclease activity is removed or reduced by defining a specific deleted (klenow-like clone, Bst polIK, which is 28 amino acids shorter at he $NH_2$-terminal end than Riggs' deleted Klenow-like fragment. Further, the Bst polIK has a start site which coincides with the $NH_2$-terminal end of the proposed Bst Klenow fragment following subtilisin digest of Bst DNA PolI to yield a Klenow fragment, and is from expression of a clone with two base mutations which were necessary to obtain translation of the deleted Klenow-like clone. Accordingly, the Bst Klenow fragment (from aa 286) is significantly different from Riggs' fragment.

While Riggs may disclose deletions in the 5'–3' exonuclease domain of the enzyme and/or its corresponding gene, and asserts that 3'–5' exonuclease activity is a "desired characteristic", Riggs does not describe or suggest DNA encoding a Bst polymerase Klenow-like fragment or a Bst polymerase Klenow-like fragment lacking 3'–5' exonuclease activity, as in the present invention. Note also again that as to other exemplified embodiments, e.g., beginning at aa 371, 453, 532 or 616, Riggs' fragment is even more significantly longer, and ergo more significantly different.

This invention in especially advantageous embodiments relates to 3' to 5' exonuclease-deficient *Bacillus stearothermophilus* (Bst) DNA polymerase, e.g., from deleted or interrupted versions of the DNApolI gene, e.g., versions having deletions at the 5' end. These deleted clones code for truncated *B. stearothermophilus* DNA polymerase enzymes that are deficient in 3' to 5' exonuclease activity. These truncated enzymes are extremely useful in nucleic acid synthesis by primer extension reactions, particularly DNA sequencing and labelling reactions.

In order to obtain these deleted clones, a fragment of the DNA polymerase I-encoding gene from *B. stearothermophilus* was obtained by PCR. This was then used as a probe to obtain a full-length gene from a Bst genomic DNA (gDNA) plasmid library. A protein was produced from this gene which gave DNA polymerase activity similar to wild-type subtilisin-treated Bst DNA polymerase. A comparison of its amino acid homology allowed an assignment of its sequences corresponding to the enzyme domains of *E. coli* DNApolI. The 3'–5' exonuclease activity is proposed to be located in a domain within the *B. stearothermophilus* DNApolI gene.

The 3' to 5' exonuclease activity of the wild type *B. stearothermophilus* DNA polymerase I was made deficient by selective deletion of amino acid residues required for the 3' to 5' exonuclease activity without inhibiting the DNA synthesis activity. The wild type Bst nucleic acid sequence was mutated at the 5' end of the gene. The mutated sequence may have a single change or multiple changes that alter the nucleotide sequence of the gene. Alterations of the DNA sequence include deletions (loss of one or more nucleotides in the DNA sequence) and/or substitutions (substituting a difference nucleotide for the original nucleotide along the DNA sequence).

The truncated *B. stearothermophilus* DNA polymerase I of this invention is preferably a recombinant protein derived from the expression of the gene for DNA polymerase from *B. stearothermophilus*; but, one can also obtain a truncated DNA polymerase I by cleaving portions of the polymerase natively expressed by Bst. The truncated *B. stearothermophilus* DNA polymerase I has an amino acid residue sequence that substantially corresponds to the amino acid residue sequence of the native *B. stearothermophilus* DNA polymerase I enzyme, with the exception of the removal or substitution of one or more amino acid residues so as to reduce or cease the 3'–5' exonuclease activity and thereby render the polymerase substantially deficient in the 3'–5' exonuclease activity. Any of a number of amino acid removal or substitutions in the subject polymerase are contemplated, so long as the requisite activity is produced. All of the purified enzymes exhibit DNA synthesis activity, but were deficient in 3' to 5' exonuclease activity.

The preparation of recombinant *B. stearothermophilus* DNApolI clones with deletions from the 5' end is further detailed in the Examples.

Specific Truncated Clones

Certain preferred embodiments of this invention relate specifically to 3' to 5' exonuclease-deficient *B. stearothermophilus* DNA polymerase I enzymes and the structural genes therefor of 1781 (PK), 1526 (P1), 1281 (P2), 1043 (P3) and 791 (P4) bp respectively; and, methods of making and using the enzymes and the genes. These clones have increasing deletions from the 5' end of the DNApolI gene and give rise to a series of truncated *B. stearothermophilus* DNA polymerase I enzymes that are deficient in 3' to 5' exonuclease activity. Using SDS-PAGE gel electrophoresis under denaturing conditions, these monomeric enzymes were determined to have molecular weights of approximately 65.6, 56.1, 47.1, 38.4 and 29.2 kDa, respectively.

The amino acid residue sequences of these truncated *B. stearothermophilus* DNA polymerase I enzymes are included FIG. 1, except that amino acid removal or substitutions are present which confer 3' to 5' exonuclease deficiency as described herein. Preferably, these preferred polymerase enzymes have an amino acid residue sequence represented by the formula shown in FIG. 1 from residue 286 (e.g., residues 1 to 285 are deleted) (Klenow—PV8168), or from residue 371 (e.g., residues 1 to 370 are deleted) (PV8169), or from residue 453 (e.g., residues 1 to 452 are deleted) (PV8170), or from residue 532 (e.g., residues 1 to 531 are deleted) (PV8171), or from residue 616 (e.g., residues 1 to 615 are deleted) (PV8172). The polymerases can culminate at residue 879 (SEQ ID NO: 3, 4, 5, 6 and 7 respectively).

Likewise, the preferred polymerases can be from expression of a Bst DNApolI gene which has had deletion, mutation, or insertional or other inactivation at the 5' end such that nucleotides from 1078 are expressed (e.g., nucleotides 1 to 1077 are deleted) or, such that nucleotides from 1333 are expressed (e.g., nucleotides 1 to 1332 are deleted), or such that nucleotides from 1578 are expressed (e.g., nucleotides 1 to 1577 are deleted), or such that nucleotides from 1816 are expressed (e.g., nucleotides 1 to 1815 are deleted), or such that nucleotides from 2068 are expressed (e.g., nucleotides 1 to 2067 are deleted) (SEQ ID NO: 8, 9, 10, 11 and 12, respectively).

The amino acid residue sequence of a truncated *B. stearothermophilus* DNA polymerase I can be determined by any suitable method, such as by automated Edman degradation, and the like.

The deleted structural genes encode truncated proteins which retain the DNA synthesis domain and but exhibit varying degrees of 3' to 5' exonuclease activity. The structural genes, comprising the clones PV8168, PV8169, PV8170, PV8171 and PV8172 may be derived from the *B. stearothermophilus* DNApolI structural gene, and is exemplified herein by the *B. stearothermophilus* DNApolI structural gene (see FIGS. 1 & 2). The DNA comprising the *B. stearothermophilus* DNApolI structural gene may be derived from genomic DNA, cDNA, synthetic DNA and combinations thereof.

The polymerases encoded by these truncated genes have at least about 75% homology with *B. stearothermophilus* DNA polymerase I, preferably at least about 90% homology, again provided that the proteins when expressed have *B. stearothermophilus* DNA polymerase I activity. Specific molecules exemplified herein include the proteins derived from the clones PV8168, PV8169, PV8170, PV8171 and PV8172, and functional derivatives thereof. A functional derivative of a DNA molecule is derived from the original DNA molecule but still may express the desired structural gene in a host or in vitro, i.e., express a gene encoding *B. stearothermophilus* DNA polymerase I activity.

These recombinant DNA molecules each have: a structural gene encoding a protein which has a processive DNA polymerase activity; a promoter heterologous to the structural gene; and an origin of replication heterologous to the structural gene. In this combination, the promoter and the structural gene are in such position and orientation with respect to each other that the structural gene may be expressed in a host cell under control of the promoter, and the origin of replication is capable of maintaining the promoter/structural gene/origin of replication combination in a host cell.

Preferably, the promoter and the origin of replication are functional in the same host cell, exemplified herein by an *E. coli* host cell. The DNA molecule is preferably contained by a host cell, exemplified herein by an *E. coli* host cell (strains JM105, XL1-Blue, BL21(DE3), BL21(DE3)pLysS and BL21(DE3)pLysE), but may, of course, exist in vitro. The promoter may be inducible, e.g. the tac promoter or the T7 promoter. The protein may also have a 3'–5' DNA exonuclease activity or may have substantially reduced 3'–5' exonuclease activity. Preferably, the structural gene is not under control of a homologous promoter. In the preferred example, the structural gene is under the control of a heterologous ribosome binding site, not a homologous ribosome-binding site.

Given the herein disclosed teachings, further detailed in the Examples, one of ordinary skill in the art can use standard recombinant DNA techniques to express *B. stearothermophilus* DNApolI or its derivatives in *E. coli*.

Other promoters, vectors, and host cells, both prokaryotic and eukaryotic, are well known in the art and in keeping with the specification, may be used to practice the invention.

The present invention specifically includes *B. stearothermophilus* DNApolI derivatives. These include genes and functional derivatives, the latter with or without enzymatic activity. A "functional derivatives" of *B. stearothermophilus* DNAPolI is a compound which possesses a biological activity (either functional or structural) that is substantially similar to a biological actual of Bst DNApolI. The term functional derivatives includes fragments, variants, analogues, or chemical derivatives of a molecule. Thus, provided that two molecules possess a similar activity, they are considered variants even if the structure of one of the molecules is not found in the other, or if the sequence of amino acid residues is not identical.

Production of Recombinant Truncated *B. Stearothermophilus* DNApolI Proteins (Cloning)

Cloning involves the use of recombinant DNA technology to propagate DNA fragments inside a foreign host. The fragments are usually isolated from chromosomes using restriction enzymes and then united with a carrier such as a vector. Following introduction into suitable host cells, the DNA fragments can then be reproduced along with the host cell DNA. Cloning provides unlimited material for experimental study.

The present invention also provides a method for production of a protein having a processive DNA polymerase activity from a host cell containing a recombinant DNA molecule under conditions where the structural gene is expressed, followed by purifying the protein expressed during the culturing step.

Production of recombinant *B. stearothermophilus* DNApolI proteins is typically produced by recombinant DNA techniques, from a gene encoding the modified enzyme. Thus, the present invention also contemplates a DNA segment consisting essentially of a sequence of nucleotide bases encoding a truncated *B. stearothermophilus* DNApolI of this invention.

Of course, modifications to the primary structure itself by deletion, addition, or alteration of the amino acids incorporated into the protein sequence during translation can be made without destroying the functionality of the protein. Such substitutions or other alterations result in proteins having an amino acid sequence encoded by DNA falling within the contemplated scope of the present invention.

Mutation can be accomplished by a variety of methods well known in the art that are not critical to the invention. Mutation methods include, but are not limited to site-directed mutation, random mutation, error-prone PCR, in vivo mutagenesis using oligonucleotides, and the like. A preferred mutation procedure has been described herein the Examples. The resulting mutated gene encodes a recombinant truncated *B. stearothermophilus* DNApolI. The mutated gene is then provided in the form of a DNA segment (excised or recovered coding sequence) that encodes the recombinant *B. stearothermophilus* DNApolI protein using standard techniques.

The invention also contemplates DNA segments that encode truncated *B. stearothermophilus* DNApolI proteins of this invention. DNA molecules, such as plasmids and bacteriophage genomes containing a DNA segment, are also a part of this invention. Host cells containing a plasmid, DNA segment, DNA molecule or bacteriophage genome of this invention are also contemplated. Preferably, a truncated *B. stearothermophilus* DNApolI-encoding DNA of this invention is in the form of a plasmid, cosmid or phage. A preferred DNA segment containing a gene that encodes a truncated *B. stearothermophilus* DNApolI is present on the plasmids PV8168, PV8169, PV8170, PV8171 and PV8172.

A preferred recombinant DNA molecule includes a nucleotide sequence shown in FIG. 1 from nucleotide base 223 to base 2859, but having various nucleotide deletions from the 5'-end according to the present invention to provide the required 3'1–5' exonuclease deficiency in the coded *B. stearothermophilus* DNApolI.

A DNA segment defining a truncated *B. stearothermophilus* DNApolI of this invention can be prepared by a variety of molecular biological techniques. The precise nucleotide sequence is not critical so long as the resulting encoded protein has the requisite properties, and preferably encodes a preferred amino acid residue sequence as described herein.

In one approach, a DNA segment can be assembled by the systematic hybridization and ligation of synthetic oligonucleotides to form the complete DNA segment. Synthetic oligonucleotides may be prepared by a variety of chemical synthetic means, such as using the triester method of Matteucci et al., 1981, J. Am. Chem. Soc. 103: 3185–3191, or using automated synthesis methods.

A recombinant DNA molecule of the present invention can be produced by operatively linking a vector to a DNA segment of the present invention.

As used herein, the term "vector" refers to a nucleic acid molecule capable of transporting between different genetic environments another nucleic acid to which it has been operatively linked. Preferred vectors are those capable of autonomous replication and/or expression of nucleic acids to which they are operatively linked are referred to herein as "expression vectors". As used herein, the term "operatively linked", in reference to DNA segments, describes that the nucleotide sequence is joined to the vector so that the sequence is under the transcriptional and translation control of the expression vector and can be expressed in a suitable host cell.

As is well known in the art, the choice of vector to which a protein encoding DNA segment of the present invention is operatively linked depends upon the functional properties desired e.g., protein expression, and upon the host cell to be transformed. These limitations are inherent in the art of constructing recombinant DNA molecules. However, a vector contemplated by the present invention is at least capable of directing the replication, and preferably also expression, of a gene operatively linked to the vector.

The methods for making a vector or recombinant can be by or analogous to the methods disclosed in U.S. Pat. Nos. 4,603,112, 4,769,330, 5,174,993, 5,505,941, 5,338,683, 5,494,807, and 4,722,848, WO 95/30018, Paoletti, "Applications of pox virus vectors to vaccination: An update," PNAS USA 93: 11349–11353, October 1996, Moss, "Genetically engineered poxviruses for recombinant gene expression, vaccination, and safety," PNAS USA 93: 11341–11348, October 1996, Smith et al., U.S. Pat. No. 4,745,051 (recombinant baculovirus), Richardson, C. D. (Editor), *Methods in Molecular Biology* 39, "Baculovirus Expression Protocols" (1995 Humana Press Inc.), Smith et al., "Production of Huma Beta Interferon in Insect Cells Infected with a Baculovirus Expression Vector," Molecular and Cellular Biology, Dec., 1983, Vol. 3, No. 12, p. 2156–2165; Pennock et al., "Strong and Regulated Expression of Escherichia coli B-Galactosidase in Infect Cells with a Baculovirus vector," Molecular and Cellular Biology Mar. 1984, Vol. 4, No. 3, p. 399–406; EPA 0 370 573, U.S. application Ser. No. 920,197, filed Oct. 16, 1986, EP Patent publication No. 265785, U.S. Pat. No. 4,769,331 (recombinant herpesvirus), Roizman, "The function of herpes simplex virus genes: A primer for genetic engineering of novel vectors," PNAS USA 93: 11307–11312, October 1996, Andreansky et al., "The application of genetically engineered herpes simplex viruses to the treatment of experimental brain tumors," PNAS USA 93: 11313–11318, October 1996, Robertson et al. "Epstein-Barr virus vectors for gene delivery to B lymphocytes," PNAS USA 93: 11334–11340, October 1996, Frolov et al., "Alphavirus-based expression vectors: Strategies and applications," PNAS USA 93: 11371–11377, October 1996, Kitson et al., J. Virol. 65, 3068–3075, 1991; U.S. Pat. Nos.5,591,439, 5,552,143, Grunhaus et al., 1992, "Adenovirus as cloning vectors," Seminars in Virology (Vol. 3) p. 237–52, 1993, Ballay et al. EMBO Journal, vol. 4, p. 3861–65, Graham, Tibtech 8, 85–87, April, 1990, Prevec et al., J. Gen Virol. 70, 429–434, PCT W091/11525, Felgner et al. (1994), J. Biol. Chem. 269, 2550–2561, Science, 259: 1745–49, 1993 and McClements et al., "Immunization with DNA vaccines encoding glycoprotein D or glycoprotein B, alone or in combination, induces protective immunity in animal models of herpes simplex virus-2 disease," PNAS USA 93: 11414–11420, October 1996, and U.S. Pat. Nos. 5,591,639, 5,589,466, and 5,580,859 relating to DNA expression vectors, inter alia. That is, the techniques of the herein cited documents can be used to express Bst DNA polymerase I, either whole or truncated, in vector systems of those documents, using the teachings herein and the knowledge in the art (e.g., as shown by documents cited herein), without any undue experimentation.

In preferred embodiments, a vector contemplated by the present invention includes a prokaryotic replicon, i.e., a DNA sequence having the ability to direct autonomous replication and maintenance of the recombinant DNA molecule extrachromosomally in a prokaryotic host cell, such as a bacterial host cell, transformed therewith. Such replicons are well known in the art.

In addition, those embodiments that include a prokaryotic replicon may also include a gene whose expression confers a selective advantage such as amino acid nutrient dependency or drug resistance to a bacterial host transformed therewith as is well known, in order to allow selection of transformed clones. Typical bacterial drug resistance genes are those that confer resistance to ampicillin, tetracycline, or kanamycin.

Those vectors that include a prokaryotic replicon may also include a prokaryotic promoter capable of directing the expression (transcription and translation) of the gene transformed therewith. A promoter is an expression control element formed by a DNA sequence that permits binding of RNA polymerase and transcription to occur. Promoter sequences compatible with bacterial hosts are typically provided in plasmid vectors containing convenient restriction sites for insertion of a DNA segment of the present invention. Bacterial expression systems, and choice and use of vectors in those systems is described in "Gene Expression Technology", Meth. Enzymol., Vol 185, Goeddel, Ed., Academic Press, N.Y. (1990) and Shatzman, A. R.,1990, Current Opinion in Biotech. 1: 5–11.

Expression vectors compatible with eukaryotic cells, preferably those compatible with vertebrate cells, can also be used to form the recombinant DNA molecules of the present invention. Eukaryotic cell expression vectors are well known in the art and are available from several commercial sources. Typically, such vectors contain convenient restriction sites for insertion of the desired gene. Typical vectors are pSVL and pKSV-10 (Pharmacia), pBPV-1/pML2d (International Biotechnologies, Inc.), and pTDT1 (ATCC, #31255).

In preferred embodiments, the eukaryotic cell expression vectors used to construct the recombinant DNA molecules of the present invention include a selectable phenotypic marker that is effective in a eukaryotic cell, such as a drug resistance selection marker or selective marker based on nutrient dependency. A preferred drug resistance marker is the gene whose expression results in neomycin resistance, i.e., the neomycin phosphotransferase (neo) gene. Southern et al., 1982, J. Mol. Appl. Genet. 1: 327–341.

The vector is used to transform a suitable host and the transformed host cultured under favorable conditions to effect the production of the recombinant B. stearothermophilus DNApolI by expression of the gene and subsequent protein production in the compatible transformed host.

The synthesized B. stearothermophilus DNApolI is isolated from the medium or from the cells. Recovery and purification of the protein may not be necessary in those instances where some impurities may be tolerated.

Each of the foregoing steps can be done in a variety of ways. For example, the desired coding sequences may be obtained from genomic fragments and used directly in appropriate hosts. The constructions for expression vectors operable in a variety of hosts are made using appropriate replicons and control sequences, as set forth below. Suitable restriction sites can, if not normally available, be added to the ends of the coding sequence so as to provide an excisable gene to insert into these vectors.

The recombinant DNA molecules of the present invention are typically introduced into host cells, via a procedure commonly known as transformation or transfection. Transformation of appropriate host cells with a recombinant DNA molecule of the present invention is accomplished by well known methods that typically depend on the type of vector used (Cohen et al., 1972, Proc. Natl. Acad. Sci. USA 69: 2110; and Maniatis et al., 1982, Molecular Cloning, A Laboratory Manual, Cold Spring Harbor Laboratory, Cold Spring Harbor, N.Y.; Rosenberg and Moss, 1990, Current Opinion in Biotech. 1: 3–4; Sorge et al., 1984, Mol. Cell. Biol. 4: 1730–37; and Wigler et al., 1979, Proc. Natl. Acad. Sci. USA 76: 1373–76). Generally, prokaryotic, yeast, insect, mammalian or plant cells are presently useful as hosts.

Prokaryotic hosts are in general the most efficient and convenient for the production of recombinant proteins and therefore are preferred for the expression of B. stearothermophilus DNApolI, and are represented by various strains of E. coli. Given the herein disclosed teachings, further detailing in the Examples, one of ordinary skill in the art can use standard recombinant DNA techniques to express B. stearothermophilus DNApolI or its derivatives in E. coli. However, other microbial strains may also be used, such as bacilli, for example, Bacillus subtilis, various species of Pseudomonas, or other bacterial strains. In such prokaryotic systems, plasmid vectors that contain replication sites and control sequences derived from species compatible with the host are used. For example, E. coli is typically transformed using derivatives of pBR322, a plasmid derived from an E. coli species by Bolivar et al., 1977, Gene 2: 95 and Sutcliffe, 1978, Nuc. Acids Res. 5: 2721–28. pBR322 contains genes for ampicillin and tetracycline resistance, and thus provides additional markers that can be either retained or destroyed in constructing the desired vector.

Commonly used prokaryotic control sequences are defined herein to include promoters for transcription initiation, optionally with an operator, along with ribosome binding site sequences. Some examples of commonly used promoters include the B-lactamase (penicillinase) and lactose (lac) promoter systems (Chang et al., 1977, Nature 198: 1056), the tryptophan (trp) promoter system (Goeddel et al., 1980, Nucleic Acids Res. 8: 4057) and the lambda-derived PL promoter (Shimatake et al., 1981, Nature 292: 28) and N-gene ribosome binding site, which has been made useful as a portable control cassette (as set forth in U.S. Pat. No. 4,711,845), which comprises a first DNA sequence that is the PL promoter operably linked to a stream of a third DNA sequence having at least one restriction site that permits cleavage with six bp 3' of the NRBS sequence.

Also useful is the phosphatase A (phoA) system described by Change et al. in European Patent Publication No. 196, 864. However, any available promoter system compatible with prokaryotes can be used. Typical bacterial plasmids are pUC8, pUC9, pBR322 and pBR329 available from Bio-Rad Laboratories, (Richmond, Calif.) and pTrc99A described herein, pPL and pkk233–2, available from Pharmacia (Piscataway, N.J.) or Clone Tech (Palo Alto, Calif.), pBluescript and pET (Stratagene, USA) and the like equivalent plasmid expression vectors. Preferred E. coli host cells include RR1, XL1-Blue (Stratagene), and the like, in addition to the equivalent host cell described herein.

In addition to bacteria, eukaryotic microbes, such as yeast, may also be used as hosts. Laboratory strains of Saccharomyces cerevisiae, Baker's yeast, are most used, although a number of other strains are commonly available. While vectors employing the two micron origin of replication are illustrated (Broach, 1983, Meth. Enz., 101: 307), other plasmid vectors suitable for yeast expression are known (see, for example, Brake et al., 1984, Proc. Natl. Acad. Sci USA 81: 4642–4647; Clarke et al., 1983 Meth. Enz. 101: 300; Halewell et al., 1987, Biotechnology 5: 363–366; Stinchcomb et al., 1979, Nature, 282: 39, Tschempe et al., 1980, Gene 10: 157). Control sequences for yeast vectors include promoters for the synthesis of glycolytic enzymes (Hess et al., 1968, J. Adv. Enzyme Reg. 7: 149; Holland et al., 1978, Biotechnology 17: 4900).

It is also possible to express genes encoding polypeptides in eukaryotic host cell cultures derived from multicellular organisms. See, for example, Tissue Culture, Academic Press, Cruz and Patterson, editors (1973). Useful host cell lines include murine myelomas N51, VERO and HeLA ccps, Chinese hamster ovary (CHO) cells available from the ATCC as CCL61, and NIH/3T3 mouse cells available from the ATCC as CRL1658. Expression vectors for such cells ordinarily include promoters and control sequences compatible with mammalian cells such as, for example, the commonly used early and late promoters from Simian Virus 40 (SV 40) (Fiers et al., 1978, Nature 273: 113), or other viral promoters such as those derived from polyoma, adenovirus 2, bovine papilloma virus, or avian sarcoma viruses, or immunoglobulin promoters and heat shock promoters.

A system for expressing DNA in mammalian systems using the HPV as a vector is disclosed in U.S. Pat. No. 4,419,446. A modification of this system is described in U.S. Pat. No. 4,601,978. General aspects of mammalian cell host system transformations have been described in U.S. Pat. No. 4,399,216.

It now appears, also, that "enhancer" regions are important in optimizing expression. Enhancer regions are sequences generally found upstream of the promoter region. Origins of replication may be obtained, if needed, from viral sources. However, integration into the chromosome is a common mechanism for DNA replication in eukaryotes.

Plant cells are also available as hosts. Control sequences compatible with plant cells such as the nopaline synthase promoter and polyadenylation signal sequences (Depicker et al., 1982, J. Mol. Appl. Gen., 1: 561) are also available. See, also, U.S. Pat. No. 4,962,028, U.S. Pat. No. 4,956,282, U.S. Pat. No. 4,886,753 and U.S. Pat. No. 4,801,540.

In addition, expression systems employing insect cells utilizing the control systems provided by baculovirus vectors have been described (Miller et al., 1986, In Genetic Engineering, Setlow, J. K. et al., eds., Plenum Publishing, Vol. 8, pp. 277–297). See, also, U.S. Pat. No. 4,745,051 and U.S. Pat. No. 4,879,236.

Infection with Agrobacterium tumefaciens (Straw et al., 1983, Gene 23: 315) is used for certain plant cells. For mammalian cells without cell walls, the calcium phosphate precipitation method of Graham and van der Eb, 1978, Virology 52: 546 is preferred. Transformations into yeast are carried out according to the method of Van Solingen et al., 1977, J. Bacteriol. 130: 946 and Hsiao, 1979, Proc. Natl. Acad Sci. USA. 76: 3829.

In addition to the transformed host cells themselves, cultures of the cells are contemplated as within the present invention. The cultures include monoclonal (clonally homogeneous) cultures, or cultures derived from a monoclonal culture, in a nutrient medium. Nutrient media useful for culturing transformed host cells are well known in the art and can be obtained from several commercial sources. In embodiments wherein the host cell is mammalian, a "serum-free" medium is preferably used.

The present method entails culturing a nutrient medium containing host cells transformed with a recombinant DNA molecule of the present invention that is capable of expressing a gene encoding a subject polypeptide. The culture is maintained for a time period sufficient for the transformed cells to express the subject polypeptide. The expressed polypeptide is then recovered from the culture. Recovery can be by techniques known in the art for isolating polymerases (Cf. Lawyer, et al., 1989).

Standard techniques of protein purification may be employed to isolate and/or further purify the polypeptide (polymerase) including: precipitation by taking advantage of the solubility at varying salt concentrations; precipitation with organic solvents, polymers and other materials; affinity precipitation and selective denaturation; column chromatography, including high performance liquid chromatography (HPLC), ion-exchange, affinity, immuno affinity or dye-ligand chromatography; immunoprecipitation; and the use of gel filtration, electrophoretic methods, ultrafiltration and isoelectric focusing. Each of the above-identified methods are well within the knowledge of the skilled artisan, and no undue experimentation is required to isolate and/or purify the polypeptides or polymerases after expression thereof by a vector or a recombinant, using the standard methodologies outlined herein, and in the literature, as well as the teachings in the Examples below.

Once a gene has been expressed in high levels, a DNA fragment containing the entire expression assembly (e.g., promoter, ribosome-binding site, and fusion protein gene) may be transferred to a plasmid that can attain very high copy numbers. For instance, the temperature-inducible "runaway replication" vector pKN402 may be used. Preferably, the plasmid selected will have additional cloning sites which allow one to score for insertion of the gene assembly. See, Bittner et al., 1981, Gene 15: 31. Bacterial cultures transformed with the plasmids are grown for a few hours to increase plasmid copy number, e.g., to more than 1000 copies per cell. Induction may be performed in some cases by elevated temperature and in other cases by addition of an inactivating agent to a repressor. Potentially very large increases in cloned truncated B. stearothermophilus DNApolI can be obtained in this way.

As described herein, the clones designated PV8168, PV8169, PV8170, PV8171, PV8172, produced using oligonucleotide PK, P1, P2, P3, P4 and a 3' primer labelled P5, were determined to retain DNA polymerase activity, and possess essentially no exonuclease activity when compared to wild type Bst DNApolI. PV8168 has been shown to retain 100% DNA polymerase activity.

Use of Deleted Clones in DNA Synthesis Reactions

The deleted clones of this invention are useful in nucleic acid synthesis by primer extension reactions, particularly DNA cycle-sequencing reactions. DNA polymerases are used to synthesize DNA molecules in the 5' to 3' direction from deoxynucleotide triphosphates (nucleotides) using a complementary template DNA strand and a primer. The DNA polymerase successively adds nucleotides to the free 3'-hydroxyl end to the growing strand.

In molecular biology, DNA polymerases used in DNA sequencing reactions generally use either 35S-, 32P- or 33P-labelled nucleotides. The proof reading or editing function of the 3' to 5' exonuclease activity of many DNA polymerases can interfere with processivity and is often disadvantageous in situations where one is trying to achieve net synthesis of DNA. The novel deleted clones having reduced or lacking such 3' to 5' exonuclease activity provided for in this invention are therefore extremely useful for DNA synthesis reactions.

Bst DNA polymerase I is a superior alternative to traditional DNA sequencing enzymes. With its 65° C. temperature optimum, reactions can be performed at elevated temperatures to reduce secondary structure in the DNA and accommodate stringent template/primer appealing conditions.

Some sequencing procedures currently involve first subcloning DNA fragments from a cosmid or bacteriophage library into special sequencing vectors that carry shorter pieces of the original cosmid fragments. The next stop is to make the subcloned fragments into sets of nested fragments differing in length by one nucleotide, so that the specific base at the end of each successive fragment is detectable after the fragments have been separated by gel electrophoresis.

Sanger et al. 1977 introduced a sequencing method using chain-terminating dideoxynucleoside triphosphates (ddNTPs). These ddNTPs differ from conventional dNTPs in that they lack a hydroxyl residue at the 3' position of deoxyribose but can be incorporated by DNA polymerases into a growing DNA chain through their 5' triphosphate groups. The absence of a 3' hydroxyl residue prevents formation of a phosphodiester bond with the succeeding dNTP. Further extension of the growing DNA chain is therefore impossible. Thus, when a small amount of one ddNTP is included with four conventional dNTPs in a reaction mixture for DNA synthesis, there is competition between extension for the chain and infrequent, but specific, termination. By using four different ddNTPs in four separate enzymatic reactions, populations of oligonucleotides are generated that terminate at positions occupied by every A, C, G, or T in the template strand. The deleted *B. stearothermophilus* polymerase clones (lacking 3' to 5' exonuclease activity) are especially suitable for such sequencing.

The Bst DNA polymerase is useful in both manual and automated radiolabeled DNA sequencing strategies. These automated DNA sequencing protocols that save laboratory time and costs while dramatically increasing power and precision.

The *B. stearothermophilus* DNAPolI has the thermostability required for automated sequencing combined with the requisite precision. Several properties of this enzyme including a high reaction temperature of 65° C., the ability to read through sequences with high G/C content, and the production of even band intensities even in multiple nucleotide runs, make Bst polymerase particularly appropriate for routine use in automated DNA sequences techniques.

Use of Bst DNApolI and of Deleted Clones in DNA Labelling Reactions

The deleted clones described in this application are also useful in DNA labelling reactions. Many molecular biological techniques require the use of DNA polymerases in DNA labelling reactions using either 35s-, 32P- or 33P-labelled nucleotides.

DNA polymerase enzymes can be used for labelling of DNA by techniques such as nick translation. Double-stranded DNA is treated with limiting amounts of DNAase I in the presence of magnesium ions. The resulting nicks serve as primers for DNA synthesis catalyzed DNA polymerase I. During synthesis, dNTP precursors are incorporated into the growing chain of DNA and the nick is translated along the DNA in a 5' to 3' direction by virtue of the 5' to 3' exonuclease activity carried by the enzyme. If radioactive precursors are supplied to the enzyme, the resulting product is radiolabeled and can be used as a hybridization probe. Bst deleted clones do not necessarily have 5'–3' exonuclease activity; and therefore, they cannot necessarily be used in nick translation. However, full length clones of Bst DNApolI may have 5'–3' exonuclease activity and may be useful in nick translation. Further, some newer nick translation techniques may not require 5' to 3' exonuclease activity and thus the technique may be useful with truncated clones of the invention.

The DNA polymerase can also be used to label the termini of DNA fragments by using $^{32}$p dNTPs to fill recessed 3' termini (end-labeling) and end labelling of DNA molecules with protruding 3' tails. The 5' and 3' termini of DNA can be radiolabeled enzymatically to yield molecules that may be used in nuclease-SI mapping of RNA, as radiolabeled primers in primer-extension reactions, and as markers of defined size in gel electrophoresis. To add distinct labels to isolated DNA molecules, DNA is copied by the DNA polymerase enzyme in the presence of nucleosides that are either radioactive or chemically tagged.

Synthetic oligonucleotides can also be labelled using the deleted clones. A short primer is hybridized to an oligonucleotide template whose sequence is the complement of the desired radiolabeled probe. The primer is then extended using the Klenow fragment to incorporate radiolabeled dNTPs in a template directed manner. After the reaction, the template and product are separated by denaturation followed by electrophoresis through a polyacrylamide gel under denaturing conditions. With this method, it is possible to generate oligonucleotide probes that contain several radioactive atoms per molecule of oligonucleotide.

Similar to DNA sequencing reactions, these polymerases can also be used in automated DNA labelling protocols. The *B. stearothermophilus* DNAPolI has the thermostability required for automated labelling combined with precision. Due to the high reaction temperature (65° C.) of the truncated Bst polymerase enzymes, the ability of the enzymes to read through sequences with high G/C content, and the production of even band intensities even in multiple nucleotide runs makes the deleted clones particularly useful in automated labelling reactions.

With respect to automated DNA sequencing or DNA labeling in which embodiments of the invention may be useful, reference is made to U.S. Pat. Nos. 5,122,345;

5,674,743; 5,556,790; 5,302,509; 5,728,529; 5,707,804; 5,688,648; 5,654,419; 5,614,386; 5,639,874; 5,674,716; 5,614,365; 5,543,026; and 5,543,018. As to automated DNA sequencing or labelling with polymerase, in which embodiments of the invention may be useful, reference is made to U.S. Pat. Nos. 5,487,972; 5,660,989; 5,523,204; 5,604,098; 5,122,345; 5,635,347; 5,210,015; 5,728,529; 5,716,784; 5,573,907; 5,302,509; 5,599,675; 5,702,888; 5,108,892; 5,723,298; 5,674,743; 5,348,853; 5,552,278; 5,593,840; and 5,674,679. See also WO 94/16107 relating to DNA sequencing with Bst polymerase.

Thus, it is believed that it is novel and nonobvious to use recombinant Bst polymerase or recombinant Klenow-like fragments from recombinant Bst polymerase or the isolated gene therefor, especially the advantageous truncated Bst polymerases (e.g., lacking or having reduced 3' to 5' exonuclease activity), as well as DNA therefor, in DNA sequencing and labelling techniques, such as automated DNA sequencing and/or labelling techniques; for instance, as shown in the documents cited herein. And therefore, the invention comprehends the use of recombinant Bst polymerase or recombinant Klenow-like fragments from recombinant Bst polymerase or the isolated gene therefor, especially the advantageous truncated Bst polymerases (lacking or having reduced 3' to 5' exonuclease activity) as well as DNA therefor, in DNA sequencing and labelling techniques.

Preparation of Hybrid Proteins

There is a need for modular DNA polymerases with defined enzymatic domains which can be used in any combination to create hybrid proteins with novel properties. The Bst DNApolI of this invention may be used in cloning and in conjunction with other clones to produce heterologous polypeptides from the clones genes.

Enzymes may consist of a single catalytic domain or of a series of independent catalytic domains linked together by a peptide backbone. One need only preserve the sequence of amino acids which forms the catalytic domains for the enzyme to function. Novel chimeric enzymes can be derived from linking together two or more catalytic domains, each retaining their enzymatic activity, to create a novel enzyme.

To create these hybrid proteins with novel properties, one or more of these deleted clones or a part thereof can be combined with other clones. In attempting to create such a novel enzyme, it may be necessary to derive modular structures form different enzymes which retain enzymatic activity (catalytic domains) and link the separate catalytic domains together to create a novel enzyme. The sequence of amino acid which forms the catalytic domain for each enzyme must be preserved during the linkage. The linkage may be achieved by gene cloning.

In the case of an enzyme with two or more catalytic domains, each of the catalytic domains must be maintained in a proper spatial relationship with respect to each other. A recombinant *B. stearothermophilus* DNApolI lacking 3'-to-5' exonuclease activity may be thus combined with other modular catalytic domains to further create other enzymes. Thus, the *B. stearothermophilus* DNApolI of this invention may be used in cloning and in conjunction with other clones to produce heterologous polypeptides from the cloned genes.

These chimeric or fusion enzymes, e.g., comprising two or more truncated Bst polymerase I enzymes (for instance from expression of DNA encoding such enzymes which was operably linked) are also useful in DNA sequencing or labelling, as are chimeric or fusion proteins comprising at least one truncated Bst polymerase I enzyme and a catalytic domain.

A better understanding of the present invention and of its many advantages will be had from the following non-limiting Examples, given by way of illustration.

EXAMPLES

Example 1
Bacterial Growth and Genomic DNA Preparation

*B. stearothermophilus* was grown at 60° C. with shaking in L-broth (10 g tryptone (Difco), 5 g yeast extract, 5 g NaCl per litre pH 7.2) (Phang et al.,1995, Gene 163: 65–68). Bacterial cells were spun down at room temperature and resuspended in 1.5 ml sucrose buffer (25% sucrose, 50 mM Tris pH 8.0). 150 μl lysozyme (10 mg/ml) was added and the mixture was left at 20° C. for 1 hr. A further 9 ml STET buffer (150 mM NaCl, 20 mM Tris pH 8.0, 1 mM EDTA pH 8.0), 1.5 ml of 5% SDS and 1.215 ml proteinase K (1 mg/ml) was added and the mixture left at 37° C. for 1 hr. 2.16 ml of 5 M NaCl and 1.8 ml of a 0.7 M NaCl/10% CTAB solution was added and the mixture was extracted with chloroform/isoamyl-alcohol and phenol/chloroform/isoamyl-alcohol. The DNA was spooled from 0.6 vol isopropanol. The DNA was washed in 70% ethanol and air-dried. The pellet was redissolved in TE buffer (20 mM Tris pH 8.0, 1 mM EDTA pH 8.0).

Example 2
Plasmid Purification

Recombinant *E. coli* clones were grown at 37° C. with shaking in L-broth with 200 μg/ml ampicillin. The transformed cells were cultured in 4 ml of L-broth overnight. 3 ml of the culture was pelleted in a microcentrifuge tube. The pellet was resuspended in 100 μl of GTE (50 mM glucose; 25 mM Tris-HCl, pH 8.0; 10 mM EDTA, pH 8.0) by vigorous vortex mixing. 200 μl of lysis buffer (0.2 M NaOH; 1% sodium dodecyl sulfate) was added immediately and the tube was inverted and mixed. 150 μl of 5 M potassium acetate (prepared by mixing 60 ml 5M potassium acetate; 11.5 ml glacial acetic acid and 28.5 ml H2O) was added and mixed quickly. The mixture was centrifuged for 1 min at 14000 rpm. The supernatant was transferred to a fresh tube and 1 ml of 95% ethanol was added. The mixture was centrifuged for 1 min at 14000 rpm. The supernatant was removed and the pellet was dried down. The plasmid DNA was resuspended in 200 μl of TE buffer (10 mM Tris-HCl, 1 mM EDTA, pH7.4) containing 20 μg/ml RNase A.

Example 3
Homology Studies to Define the Approximate Location and Size of the DNA Synthesis Domain The amino acid sequence of the 3'–5' exonuclease domain of *E. coli* DNApolI was used to locate a similar domain for *Bacillus subtilis* DNApolI (Barnes et al., 1992, Gene 111: 43–49). Similarly the 3'–5' exonuclease domain of the *B. stearothermophilus* DNApolI can be located using *E. coli* DNApolI as the basis for comparison (Ito and Braithwaite, 1991, Nucleic Acids Res. 19: 4045–4057). This was done by using a computer program (DNASIS V2.0) to compare the amino acid sequences. There is a 42% match between the two sequences. Sequence homology in *B. stearothermophilus* DNApolI appears to begin around 436 amino acid (aa) residue and ends at the 954 amino acid residue. This gives a Klenow-like fragment for *B. stearothermophilus* DNApolI of about 518 amino acids, which is much shorter than the 600 amino acid expected for this family (Joyce, 1991, Current Opinion in Structural Biol. 1: 123–129).

By comparing the peptide sequences of various DNA-dependent polymerases, three conserved segments termed Exo I, Exo II, and Exo III, have been proposed to be located in the 3'–5' exonuclease domain and, thus define the extent of the 3'–5' exonuclease domain to consist of about 207 amino acids extending from the 350 to 557 residues in *E. coli* DNApolI (Blanco et al., 1992, Gene 112: 139–144; Reha-Krantz, 1992, Gene 112: 133–137). Yet another reference (Steitz and Joyce, 1987, In Protein Engineering, Chapt. 20, pp. 227–235. Oxender, D. A., and Fox, C. F. (eds). Alan R. Liss, New York), drawing its conclusion from X-ray crystallography, has indicated that the exonuclease domain of the *E. coli* DNApolIK fragment is expected to be about 193 amino acids in length, extending from 324 to 517 aa residue.

Thus, there are uncertainties as to the exact size and siting of the various domains. In view of this, a series of primers were designed to clone a series of 5' deleted *B. stearothermophilus* DNApolI clones using polymerase chain reaction (PCR). These series of 5' deleted clones will increasingly define the DNA synthesis domain.

Example 4

Designing of Primers and Production of the Deleted Genes

Primers were from Genosys, USA. All restriction enzymes were from New England Biolabs, USA. T4 DNA ligase was from Promega, USA. Taq polymerase was from Promega, USA, and the radioactive nucleotides were from NEN-Dupont, USA.

The main concern of primer design here is to maintain the correct reading frame (Innis et al., 1990, "PCR Protocols: A Guide to Methods and Applications". Academic Press, San Diego). In this case, either of the vectors exemplified here, pTrc99A or pET11d, has an engineered NcoI restriction site in frame for translation starting with the ATG codon which has been aligned with the *E. coli* ribosome binding site. Thus, cloning of the 5' end of the gene into this NcoI restriction site would immediately aligned it in the right reading frame for translation to occur.

As the 5' end of the *B. stearothermophilus* DNApolI gene is to be deleted in a sequential series, the 5' end primers must be designed to introduce a NcoI restriction site as well as to prime to the designated sites. After DNA amplification, the amplified clones are digested with NcoI restriction enzyme to create sticky ends suitable for cloning into the vector. The 5' end primers are designated PK, P1, P2, P3 and P4 and their priming sites are indicated in FIG. 1.

The 5' end primers are:

P1: 5'-CAT GCC /ATG/ GTT GAT TCA AAG CGG GCG G-3' (SEQ ID NO: 13)

P2: 5'-CAT GCC /ATG/ GCG GCG GCG ATT TGG-3' (SEQ ID NO: 14)

P3: 5'-CAT GCC /ATG/ GCG CCA AAA CAG CTC GGG-3' (SEQ ID NO: 15)

P4: 5'-CAT GCC /ATG/ GGC CGC CTC AGC TC-3' (SEQ ID NO: 16)

PK: 5'-CAT GCC /ATG/ GCC GTC CAA-3' (SEQ ID NO: 17)

The sequence which has been underlined is the NcoI restriction site and the boxed and bold sequence (/ATG/)is the translation start. Some bases have been altered to enhance hybridization as in a silent mutation while maintaining the peptide sequence.

Translation initiation has been known to be affected by the formation of base-paired secondary structures. It has been possible to correlate low or no protein synthesis with proposed mRNA secondary structures that involve either the initiating AUG codon or the Shine-Dalgarno sequence (Buell et al., 1985; Iserentant and Fiers, 1980; Reznikoff and Gold, 1986) and this has been clearly shown by the disruption of the mRNA secondary structures around the AUG start site for effective translation (Devlin et al., 1988; Gheysen et al., 1982; Hall et al., 1982; Schoner et al., 1984). The computer program (DNASIS V2.0) was also used to predict possible mRNA 5' secondary structures of the designed primers to avoid mistranslation.

Thus, using computer models of various previously cloned genes, we found good correlation of protein synthesis to the predicted 5' end mRNA secondary structures. In general, thermodynamic values of about –2.0 kcal/mol or greater appeared to be favorable for protein synthesis. All the 5' end primers were designed based on these rationalizations.

The primer for the 3' end of the gene is the same for all the deleted clones. It may be any priming site located in a 3' position to the internal NcoI site. In this example, the 3' end primer was located on the pTrc99A vector itself within the multicloning region (see FIG. 2). A large 3' end fragment of the *B. stearothermophilus* DNApolI gene had been cloned into this vector as described in Phang et al. (1995). This was termed PV8168. Thus DNA amplification was performed directly on this plasmid clone.

The 3' end primer is:

P5: 5'-GCTTGCATGCCTGCAGGTCG-3' (SEQ ID NO: 11)

Example 5

Cloning of 5' Deleted *B. stearothermophilus* DNApolI genes

In vitro DNA manipulations were done by standard procedures (Berger, S.L. et al., 1987, "Guide to Molecular Cloning Techniques" Meth. Enz. 152: 393–399, 415–423, 432–449, 661–704; Sambrook et al., 1989, In Molecular Cloning: A Laboratory Manual, 2nd Ed. Cold Spring Harbour Press, New York). Restriction enzymes were from New England Biolabs, USA, and T4 DNA ligase was from Promega, USA. In this example, pTrc99A vector (Pharmacia Biotech, Sweden) will be used to describe a general scheme for cloning of all the 5' deleted genes. Placement of the *B. stearothermophilus* DNApolI gene under control of a trc promoter took advantage of Nco I site covering the ATG translational start sites of the pTrc99A vector (Phang et al., 1995).

The expression vector pTrc99A contains a strong trc promoter that, when induced, will result in the overexpression of the protein. This promoter is controlled by the laciq repressor. Thus glucose must be added to the culture media to repress the basal level of expression in the uninduced state. Induction occurs with the addition of lmM IPTG (Amann et al., 1988, Gene 69: 301–315).

However as there is an internal NcoI restriction site in the *B. stearothermophilus* DNApolI gene (Phang, 1995), it was necessary to insert the gene into the pTrc99A vector in two stages.

Figure 3:
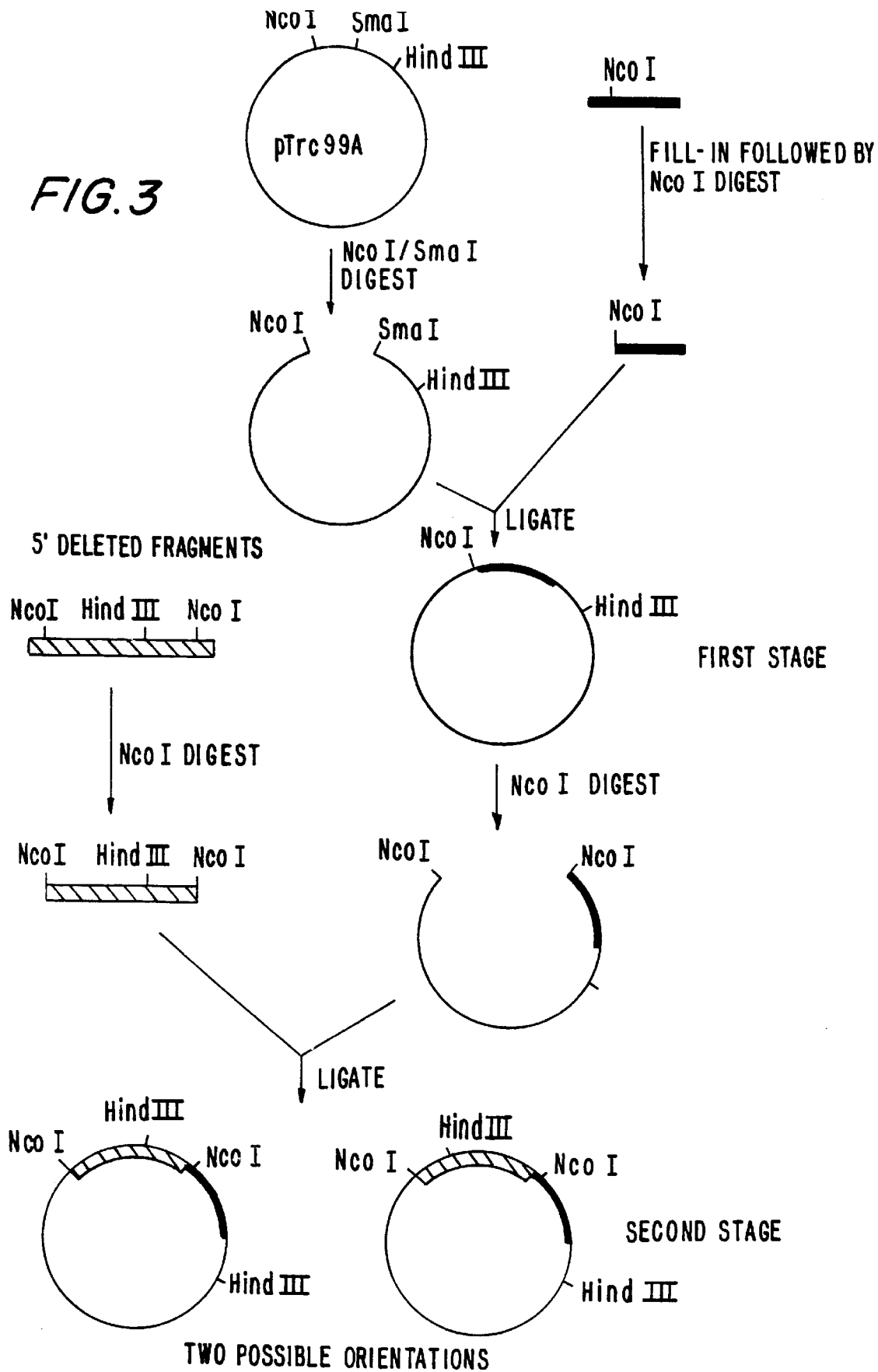

The first stage involves cloning the 3' end into the vector and this construct may be used to clone all the 5' deleted clones in the second stage (FIG. 3). A 3' end fragment of the *B. stearothermophilus* DNApolI gene spanning the internal NcoI restriction site was digested with NcoI restriction enzyme and directionally cloned into the pTrc99A vector pre-digested with NcoI+SmaI restriction enzymes. This heterologous construct was now digested with NcoI to accept the 5' deleted primers. The second stage involves the cloning of the various 5' end fragments into the first stage construct. The 5' deleted *B. stearothermophilus* DNApolI genes spanning the 5' end priming sites to the end of the gene was amplified and digested with NcoI. The 5' end fragments were ligated to the first stage construct. Orientation was checked by either digesting the recombinant with HindIII or DNA sequencing. The correct deleted clone should result in overexpression and synthesis of the correct truncated proteins.

Example 6
IPTG Induction of Recombinant Clones

Clones were grown up at 37° C. overnight in L-broth with 1% glucose and 200 μg/ml ampicillin. The following day, a 4 ml aliquot of culture was seeded into 200 ml of L-broth with 200 μg/ml ampicillin and grown at 37° C. until 0.8 O.D.600. The culture was induced with IPTG (1 mM final concentration) and further grown at 30° C. for 3 hours.

As we are attempting to eliminate the various possibilities for the lack of protein production, we need to abolish basal level synthesis of the protein in the control samples. It has been previously shown (Silverstone et al., 1970, Proc. Natl. Acad. Sci. USA 66: 773–778) that the lacUV5 promoter is insensitive to glucose repression of up to 0.4%; thus basal levels of B. stearothermophilus DNApolI was also obtained in our controls (0.1% glucose). An empirical assay was performed on overnight cultures of recombinants grown in various glucose concentrations. A 1% glucose concentration was used in subsequent experiments.

Clones were grown up at 37° C. overnight in LB medium with 1 glucose to repress constitutive expression from the trp/lac promoter, and 200 μg/ml ampicillin was added as a precaution. The following day, a 4 ml aliquot was seeded into 200 ml of LB with ampicillin and grown until A600 nm=0.8. IPTG was added to a final concentration of 1 mM and induced at 30° C. for 3 hrs. This was spun down and resuspended in 40 ml 10 mM Tris pH7.5. The pellet was stored overnight at −20° C. Overnight samples were pelleted and resuspended in 10 ml of 10 mM Tris pH7.5. This was sonicated at 8–10 W with a Vibra-cell (Sonics & Materials, Connecticut, USA), 10× each round for 1 min. The mixture was incubated at 60° C. for 15 mins to denature the E. coli proteins and centrifuged at 12500 rpm for 10 mins to collect a clear supernatant (Engelke, 1990; Laywer, 1989; Phang, 1995).

Example 7
SDS-PAGE Gel Electrophoresis

The molecular weight of the dialyzed product may be determined by any technique, for example, by sodium dodecylsulfate-polyacrylamide gel electrophoresis (SDS-PAGE) using protein molecular weight markers. The series of truncated B. stearothermophilus DNApolI enzymes that are deficient in 3'-5' exonuclease activity purified by the above method in EXAMPLE 5 have relative molecular weights, determined by SDS-PAGE under denaturing conditions, of about 65.6, 56.1, 47.1, 38.4, and 29.2 kDa.

Samples were analyzed with the Bio-Rad Mini-Protein II Apparatus to check for protein synthesis (Hames and Rickwood, 1989, In Gel Electrophoresis of Proteins: A Practical Approach, IRL, Oxford). 1 ml of cell sample was pelleted and resuspended in 100 μl Laemmli buffer (0.05 M DTT, 0.125 M Tris pH 6.8, 50% glycerol (v/v), 0.05% bromophenol blue (w/v), 1% SDS). The mixture was boiled for 5 min, and centrifuged at 14000 rpm for 5 min. 20 μl of the supernatant was loaded onto 12% acrylamide gels with a 5% stacking gel and electrophoresed at 120 V for 60–90 min, then at constant current 20 mamp for 1 hour in Tris/glycine/SDS buffer (25 mM Tris pH 8.3, 192 mM glycine, 0.1% SDS). Gels were stained in Coomassie Blue (0.1% Coomassie Blue R-250 (w/v), 10% acetic acid, 45% methanol, 45% H2O) for 2 hr. then destained (10% acetic acid, 45% methanol, 45% H2O) and dried down in a vacuum at 60° C. for 2 hrs between two pieces of wet cellophane.

Example 8
Assay for B. stearothermophilus DNApolI Activity

The collected fractions were separately assayed for DNA polymerase I activity (Setlow et al., 1972, J. Biol. Chem. 247: 224–231; Setlow and Kornberg, 1972, J. Biol. Chem. 247: 232–240). The reaction mix contained 20 mM Tris pH 8.5, 20 mM MgCl2, 1 mM each dCTP, dGTP, dTTP, 1.25 μg/μl activated DNA (Pharmacia), 1000–15000 Ci/mM [35S]-dATP, 1–10 units of enzyme, and water to 0.3 ml. The assay is initiated by the addition of enzyme, and the mixtures were incubated for 5 mins at 65° C. The reaction was stopped by addition of 1 ml chilled 10% TCA/50 mM sodium pyrophosphate. After 10 minutes at 4° C., the solution was filtered through a glass fibre (Whatman GF/C, 2.4 cm), washed 5 times with 5 ml chilled 10% TCA/50 mM sodium pyrophosphate, and then 3 times with 5 ml ethanol. The filters were dried under suction for two minutes and then counted in a scintillation counter. An incubation without enzyme is included in each set of assay (One unit of polymerase activity catalyzes the incorporation of 10 nmol total nucleotides into a DEAE-precipitable form in 30 minutes at 72° C.) As described herein, the clones designated PV8168, PV8169, PV8170, PV8171, PV8172, were determined to retain their DNA polymerase activity when compared to wild type B. stearothermophilus DNApolI. Indeed, PV8168 retained 100% of its DNA polymerase activity.

Example 9
DNA Sequencing

DNA Sequencing Reactions:
1. Mix the following in a 1.5 ml microcentrifuge tube:

| 5x Reaction Buffer | 2.0 μl | |
|---|---|---|
| primer | 1.0 μl | (2.5–5.0 ng) |
| ssDNA template | | (250–500 ng) |
| dH$_2$O | to 10 μl | |

2. Place in a 75° C. water bath for 5 minutes, then cool slowly to room temperature (about 5 minutes). Note: this step is optional for single-strand templates only, and it can be omitted.

3. During the annealing, label 4 tubes "A", "C", "G", and "T"; add 2.0 μl of each pre-mixed nucleotide solution to the respective tube, and pre-warm to 65° C.

4. Add to the annealed reaction (from step 2):

Bst DNA polymerase 1.0 μl (1.0 unit)

[a-35S]dATP 1.5 μl

Mix gently, spin 2–3 seconds in a microcentrifuge, and aliquot 2.5 μl to each of the tubes (from step 3).

5. Incubate at 65° C. for 2 minutes.

6. Dilute 1.0 μl of 20× Chase Solution into 19 μl of water, 8.0 μl of diluted Chase is needed per reaction set.

7. Add 2.0 μl of diluted Chase to each tube, mix gently, and incubate at 65° C. for 2 minutes.

8. Stop the reactions by adding 4.0 μl of Stop Solution.

9. Denature the samples at >75° C. for 1–2 minutes immediately prior to loading.

Double Strand Template (Plasmid) Sequencing Protocol

1. Mix the following in a 1.5 ml microcentrifuge tube:
   dsDNA template 10 μl (1–3 μg) 0.4N NaOH, 0.4 mM EDTA 10 μl 2. Incubate at 75° C. for 5 minutes.

3. Add 2.0 μl of 3 M ammonium acetate, pH 5.2, and 50 μl of cold ethanol. Place tube in −80° C. for 15 minutes.

4. Spin in a microcentrifuge at 12,000 rpm, 4° C. for 5 minutes.

5. Wash pellet with 200 µl of cold 70% ethanol. Spin 2–3 minutes and remove the supernatant. Note: this step is optional and may be omitted.
6. Dry pellet under vacuum for 3–5 minutes, then resuspend in 7.0 µl TE.
7. Proceed with annealing and sequencing as described above.

Polyacrylamide sequencing gels were prepared (6% gel having 5.7% acrylamide 0.3% bis-acrylamide/7M Urea/1X TBE), preheated to 50° C., using a power supply regulated to 120 watts (W). The denatured sample (2 µl) was loaded onto the gel and electrophoresed at 55° C. until the bromophenol blue dye front migrated to the bottom of the gel. The gel assembly was taken apart, the gel transferred to Whatmann 3 MM paper, dried and exposed to X-ray film for 12–20 hrs.

Example 10
Large Scale Production and Purification of the Recombinant Truncated B. stearothermophilus DNApolI Proteins An overnight culture of E. coli clones in sterile LB containing 100 µg/ml ampicillin and 34 µg/ml chloramphenicol was seeded 1:50 in a 1 L Belco culture flask containing 100 µg/ml ampicillin. This was shaken at 37° C., 250 rpm until OD600 reached 0.6. This was induced with 1 mM IPTG and shaken for another 3 hrs at 30° C. The sample was spun at 8000 rpm, 4° C. for 5 minutes. The supernatant was discarded and the pellet was stored in −20° C. The pellet was resuspended in 25–30 ml 10 mM Tris pH 7.5 per falcon tube and 0.02 mM PMSF was added to the cell suspension. This was sonicated at 8–10 W with a Vibra-cell (Sonics & Materials, Connecticut, USA),10× each round for 1 min. The sonicated cell suspension was incubated in 60° C. for 15 min. The sample was centrifuged in a JA-20 (Beckmann, USA), 13000 rpm for 30 min at 4° C. The clear supernatant was loaded onto an ion-exchange DE-52 chromatographic column using 10 mM Tris pH 7.5 as buffer and eluted in a gradient (0–0.3 M NaCl) over 80 fractions (6 ml each). Purified fractions were checked on SDS-PAGE for protein concentrations (Deutscher, M. P. , 1990, Meth. Enz. 182: 738–751). Typically, the purified protein is dialyzed after purification against a low salt buffer, e.g., 10 mM Tris pH 7.5, 1 mM dithiothreitol. Typically, a stabilizing agent, such as glycerol, is added to the preparation to facilitate low temperature storage of the purified, recombinant enzyme.

In preferred embodiments, B. stearothermophilus DNApolI is used in combination with a thermostable buffer such as 20 mM Tris pH 8.5, 20 mM MgCl2, 1 mM each dCTP, dGTP, dTTP, 1.25 µg/µl activated DNA (Pharmacia), 1000–15000 Ci/mM [35S]-dATP. Thus, the invention also contemplates compositions containing an enzymatically active amount of an Bst DNA polymerase in a compatible buffer.

Production of recombinant B. stearothermophilus DNApolI proteins is typically produced by recombinant DNA techniques from a gene encoding the modified enzyme. The precise nucleotide sequence is not critical as long as the resulting encoded protein has the requisite properties.

The DNA segment can then be operatively linked to a vector to create a recombinant DNA molecule using well known techniques. The nucleotide sequence is joined to the vector so that the sequence is under the transcriptional and translational control of the expression vector. The vector is then used to transform a suitable host and the transformed host is cultured under favorable conditions to effect the production of the recombinant B. stearothermophilus DNApolI by expression of the gene and subsequent protein production in the compatible transformed host. The details of the recombinant techniques and the transformation of cells are provided above and use techniques that are well known to the skilled artisan.

Having thus described in detail preferred embodiments of the present invention, it is to be understood that the invention defined by the appended claims is not to be limited to particular details set forth in the above description as many apparent variations thereof are possible without departing from the spirit or scope of the present invention.

DOCUMENT LIST

U.S. Pat. No. 5,489,523 2/1996 Mathur et al.
Amann, E., Ochs, B. and Abel, K.-J., 1988, "Tightly regulated tac promoter vectors useful for the expression of unfused and fused proteins in *Escherichia coli*". Gene 69: 301–315.
Barnes, M. H., Hammond, R. A., Kennedy, C. C., Mack, S. L. and Brown, N. C., 1992, "Localization of the exonuclease and polymerase domains of *Bacillus subtilis* DNA polymerase III". Gene 111: 43–49.
Berger, S. L. et al., 1987, "Guide to Molecular Cloning Techniques" Meth. Enz. 152: 393–399, 415–423, 432–449, 661–704.
Bernat, A. et al., 1989, "A Conserved 3'–5' Exonuclease Active . . . " Cell 59: 219–228.
Bittner et al., 1981, Gene 15: 31.
Blanco, L., Bernard, A. and Salas, M., 1992, "Evidence favouring the hypothesis of a conserved 3'–5' exonuclease active site in DNA-dependent DNA polymerases". Gene 112: 139–144.
Bolivar et al., 1977, Gene 2: 95
Bradford, 1976, Anal. Biochem. 72: 248.
Brake et al., 1984, Proc. Natl. Acad. Sci USA 81: 4642–4647.
BRL 1989 Catalogue & Reference Guide, page 5
Broach, 1983, Meth. Enz., 101: 307.
Brown, W. E., Stump, K. H. and Kelly, W. S., 1982, "Escherichia coli DNA polymerase I". J Biol. Chem. 257: 1965–1972.
Buell, G., Schulz, M. F., Selzer, G., Chollet, A., Movva, N. R., Simon, D., Escanez, S. and Kawashima, 1985, "Optimizing the expression in *E. coli* of a synthetic gene encoding somatomedin-C (IGF-I)". Nucleic Acids Res. 13: 1923–1938.
Chang et al., 1977, Nature 198: 1056
Clarke et al., 1983 Meth. Enz. 101: 300
Cohen et al., 1972, Proc. Natl. Acad. Sci. USA 69: 2110.
Cowart, M., Gibson, K. J., Allen, D. J. and Benkovic, S. J., 1988, "DNA substrate structural requirements for the exonuclease and polymerase activities of prokaryotic and phage DNA polymerases". Biochem. 20: 1973–1983.
Depicker et al., 1982, J. Mol. Appl. Gen., 1: 561.
Deutscher, M. P. , 1990, "Guide to Protein Purification". Meth. Enz. 182: 738–751.
Devlin, P. E., Drummond, R. J., Toy, P., Mark, D. F., Watt, K. W. K., and Devlin, J. J. (1988) "Alteration of amino-terminal codons of human granulocyte-colony-stimulating factor increases expression levels and allows efficient processing by methionine aminopeptidase in *Escherichia coli*". Gene 65: 13–22.
Engelke, D. R., Kriskos, A., Bruck, M. E., Ginsbury, D. N. A., 1990, "Purification of Thermus aquaticus DNA polymerase expressed in *Escherichia coli*". Anal. Chem. 191: 396–400.
Fiers et al., 1978, Nature 273: 113

Frey, M. W., Nossal, N. G., Capson, T. L. and Benkovic, S. J., 1992, "Construction and characterization of a bacteriophage T4 DNA polymerase deficient in 3'–5' exonuclease activity". Proc. Natl. Acad. Sci. USA 90: 2579–2583.

Gheysen, D., Iserentant, D., Derom, C., and Fiers, W.,1982, "Systematic alteration of the nucleotide sequence preceding the translation initiation codon and the effects on bacterial expression of the cloned SV40 small-t antigen gene". Gene 17: 55–63.

Goeddel et al., 1980, Nucleic Acids Res. 8: 4057

Graham and van der Eb, 1978, Virology 52: 546.

Halewell et al., 1987, Biotechnology 5: 363–366.

Hall, M. N., Gabay, J., Debarbouille, M., and Schwartz, M., 1982, "A role for mRNA secondary structure in the control of translation initiation". Nature 295: 616–618.

Hames, B. D., and Rickwood, D., 1989, "Gel Electrophoresis of Proteins. A Practical Approach". IRL, Oxford.

Hess et al., 1968, J. Adv. Enzyme Reg. 7: 149.

Holland et al., 1978, Biotechnology 17: 4900.

Hsiao,1979, Proc. Natl. Acad Sci. USA. 76: 3829

Innis, M. A., Gelfand, D. H., Sninsky, J. J., and White, T. J., 1990, "PCR Protocols: A Guide to Methods and Applications". Academic Press, San Diego.

Iserentant, D., and Fiers, W., 1980, "Secondary structure of mRNA and efficiency of translation initiation". Gene 9: 1–12.

Ito, J. and Braithwaite, D. K., 1991, "Compilation and alignment of DNA polymerase sequences". Nucleic Acids Res. 19: 4045–4057.

Joyce, C. M., 1991, "Can DNA polymerase I (Klenow fragment) serve as a model for other polymerases?" Current Opinion in Structural Biol. 1: 123–129.

Joyce, C. M., Kelley, W. S., and Grindley, N. D. F., 1982, "Nucleotide sequence of the *Escherichia coli* polA gene and primary structure of DNA polymerase I". J. Biol. Chem. 257: 1958–1964.

Joyce, C. M., Kelley, W. S., and Grindley, N. D. F., 1983, "Construction of a plasmid that overproduces the large proteolytic fragment (Klenow fragment) of DNA polymerase I of *Escherichia coli*". Proc. Natl. Acad. Sci. USA 80: 1830–1834.

Kaboev et al., 1981, J. Bacteriol. 145: 21–26

Klenow, H. and Henningsen, I., 1970, "Selective elimination of the exonuclease activity of the DNA polymerase from *E. coli* by limited proteolysis". Proc. Natl. Acad. Sci. USA 65: 168–175.

Kornberg, A., 1974, In DNA Synthesis. W. H. Freeman, San Francisco.

Lawyer, F. C., Stoffel, S., Saiki, R. K., Myambo, K., Drummond, R. and Gelfand, D. H., 1989, "Isolation, characterization, and expression in *Escherichia coli* of the DNA polymerase gene from Thermus aquaticus". J. Biol. Chem. 264: 6427–6437, Leavitt et al., 1989, "T5 DNA Polymerase: Structural-Functional Relationships to Other DNA Polymerases", Proc. Natl. Acad. Sci USA 86: 4465–4469.

Lu, Y.Y., Ye, S. Y. and Hong, G. F., 1991, "Large fragment of DNA polymerase I from *Bacillus stearothermophilus* (Bst polymerase) is stable at ambient temperature". BioTechniques 11: 465–466.

Maniatis et al., 1982, Molecular Cloning, A Laboratory Manual, Cold Spring Harbor Laboratory, Cold Spring Harbor, N.Y.

Matteucci et al., 1981, J. Am. Chem. Soc. 103: 3185–3191

McClary, J., Ye, S. Y., Hong, G. F., Witney, F., 1991, "Sequencing with the large fragment of DNA polymerase I from *Bacillus stearothermophilus*". DNA Sequence 1: 173–180.

Mead, D. A., McClary, J. A., Luckey, J. A., Kostichka, A. J., Witney, F. R. and Smith, L. M., 1991, "Bst DNA polymerase permits rapid sequence analysis from nanogram amounts of template". Biotechniques 11: 76–87.

Miller et al., 1986, In Genetic Engineering, Setlow, J. K. et al., eds., Plenum Publishing, Vol. 8, pp. 277–297.

Morrison et al., 1991, Proc. Natl. Acad Sci. USA 88: 9473–9477.

Ollis, D.L., Brick, P., Hamlin, R., Xuong, N. G. and Steitz, T. A., 1985, "Structure of large fragment of *E. coli* DNA polymerase I complexed with dTMP". Nature 313: 762–766.

Phang, S. M., Teo, C. Y., Lo, E., and Wong, V. W. T., 1995, "Cloning and complete sequence of the DNA polymerase-encoding gene (BstpolI) and characterisation of the Klenow-like fragment from *Bacillus stearothermophilus*". Gene 163: 65–68.

Reha-Krantz, L. J., 1992, "Are there highly conserved DNA polymerase 3'–5' exonuclease motifs?" Gene 112: 133–137.

Reznikoff, W. and Gold, L., 1986, "Maximising Gene Expression", Butterworths, Boston, Mass.

Rosenberg, M. and Moss, B., 1990, "Expression systems, Editorial overview". Current Opinion in Biotech. 1: 3–4.

Sambrook, J., Fritsch, E. F., and Maniatis, T., 1989, "Molecular Cloning: A Laboratory Manual, 2nd Ed". Cold Spring Harbour Press, New York.

Schauder, B., and McCarthy, J., 1989, "The role of bases upstream of the Shine-Dalgarno region and in the coding sequence in the control of gene expression in *E. coli*: translation and stability of mRNAs in vivo". Gene 78: 59–72.

Schoner, B. E., Hsiung, H. M., Belagaje, R. M., Mayne, N. G., and

Schoner, R. G., 1984, "Role of mRNA translational efficiency in bovine growth hormone expression in Escherichia coli". Proc. Natl. Sci. USA 88: 5403–5407.

Setlow, P. et al., 1972, "Deoxyribonucleic acid polymerase: I. Two distinct enzymes in one polypeptide". J. Biol. Chem. 247: 224–231.

Setlow, P. and Kornberg, A., 1972, "Deoxyribonucleic acid polymerase: II. Two distinct enzymes in one polypeptide". J. Biol. Chem. 247: 232–240.

Shatzman, A. R.,1990, "Gene expression using Gram-negative bacteria". Current Opinion in Biotech. 1: 5–11.

Shimatake et al., 1981, Nature 292: 28

Silverstone et al., 1970, Proc. Natl. Acad. Sci. USA 66: 773–778.

Sorge et al., 1984, Mol. Cell. Biol. 4: 1730–37.

Southern et al., 1982, J. Mol. Appl. Genet. 1: 327–341.

Spacciapoli, P. and Nossal, N. G., 1994, "A single mutation in bacteriophage T4 DNA polymerase (A737V, tsL141) decreases its processivity as a polymerase and increases its processivity as a 3'–5' exonuclease". J. Biol. Chem. 269: 438–446.

Steitz, T. A., and Joyce, C., 1987, "Exploring DNA polymerase I of *E. coli* using genetics and x-ray crystallography". In Protein Engineering, Chapt. 20, pp. 227–235. Oxender, D. A., and Fox, C. F. (eds). Alan R. Liss, New York.

Stenesh and Roe, 1972, Biochim. Biophys. Acta 272: 156–166

Stinchcomb et al., 1979, Nature, 282: 39

Straw et al., 1983, Gene 23: 315.

Sutcliffe, 1978, Nuc. Acids Res. 5: 2721–28.

Tschempe et al., 1980, Gene 10: 157.

Ye, S. Y. and Hong, G. F., 1987, "Heat-stable DNA polymerase I large fragment resolves hairpin structure in DNA sequencing". Scientia Sinica 30: 503–506.

What is claimed is:

1. An isolated nucleic acid molecule encoding a *Bacillus stearothermophilus* DNA polymerase I enzyme having reduced 3' to 5' exonuclease activity which comprises SEQ ID NO: 1.

2. An isolated nucleic acid molecule encoding a *Bacillus stearothermophilus* DNA polymerase I having reduced 3' to 5' exonuclease activity comprising SEQ ID NO: 1 having deletions, inactivating insertions, or mutations in the 5' end of the molecule in the region from nucleotides 1 to 2067.

3. An isolated DNA molecule comprising a nucleotide sequence as in FIG. 1 (SEQ ID NO: 1) having deletions in the 5' end of the molecule such that the DNA molecule encodes an enzyme which retains DNA synthesis activity but is deficient in 3' to 5' exonuclease activity in the region from nucleotides 1 to 2067.

4. The isolated DNA molecule of claim 3, wherein nucleotides 1 to 1077 of FIG. 1 (SEQ ID NO: 1) are deleted.

5. The isolated DNA molecule of claim 3, which begins at nucleotide 1078 of FIG. 1 (SEQ ID NO: 1).

6. The isolated DNA molecule of claim 3, wherein nucleotides 1 to 1332 of FIG. 1 (SEQ ID NO: 1) are deleted.

7. The isolated DNA molecule of claim 3, which begins at nucleotide 1333 of FIG. 1 (SEQ ID NO: 1).

8. The isolated DNA molecule of claim 3, wherein nucleotides 1 to 1577 of FIG. 1 (SEQ ID NO: 1) are deleted.

9. The isolated DNA molecule of claim 3, which begins at nucleotide 1578 of FIG. 1 (SEQ ID NO: 1).

10. The isolated DNA molecule of claim 3, wherein nucleotides 1 to 1815 of FIG. 1 (SEQ ID NO: 1) are deleted.

11. The isolated DNA molecule of claim 3, which begins at nucleotide 1816 of FIG. 1 (SEQ ID NO: 1).

12. The isolated DNA molecule of claim 3, wherein nucleotides 1 to 2067 of FIG. 1 (SEQ ID NO: 1) are deleted.

13. The isolated DNA molecule of claim 3, which begins at nucleotide 2068 of FIG. 1 (SEQ ID NO: 1).

14. The isolated DNA molecule of claim 2, encoding a DNA polymerase of FIG. 1 (SEQ ID NO: 2) wherein amino acids 1 to 285 are deleted.

15. The isolated DNA molecule of claim 2, encoding a DNA pol merase which begins at amino acid 286 of FIG. 1 (SEQ ID NO: 2).

16. The isolated DNA molecule of claim 2, encoding a DNA polymerase of FIG. 1 (SEQ ID NO: 2) wherein amino acids 1 to 370 are deleted.

17. The isolated DNA molecule of claim 2, encoding a DNA polymerase which begins at amino acid 371 of FIG. 1 (SEQ ID NO: 2).

18. The isolated DNA molecule of claim 2, encoding a DNA polymerase of FIG. 1 (SEQ ID NO: 2) wherein amino acids 1 to 452 are deleted.

19. The isolated DNA molecule of claim 2, encoding a DNA nolymerase which begins at amino acid 453 of FIG. 1 (SEQ ID NO: 2).

20. The isolated DNA molecule of claim 2, encoding a DNA polymerase of FIG. 1 (SEQ ID NO: 2) wherein amino acids 1 to 531 are deleted.

21. The isolated DNA molecule of claim 2, encoding a DNA polymerase which begins at amino acid 532 of FIG. 1 (SEQ ID NO: 2).

22. The isolated DNA molecule of claim 2, encoding a DNA polymerase of FIG. 1 (SEQ ID NO: 2) wherein amino acids 1 to 615 are deleted.

23. The isolated DNA molecule of claim 2, encoding a DNA polymerase which begins at amino acid 616 of FIG. 1 (SEQ ID NO: 2).

24. The isolated DNA molecule of any one of claims 14, 15, 16, 17, 18, 19, 20, 21, 22, or 23, wherein the DNA polymerase enzyme retains DNA synthesis activity but is deficient in 3' to 5' exonuclease activity.

25. A method for producing a *Bacillus stearothermophilus* DNA polynicrase I having a processive DNA synthesis activity and a substantially reduced 3'–5' exonuclease activity comprising the steps of:

(1) isolating a DNA encoding DNA polymerase I enzyme from *Bacillus stearothermophilus;*

(2) deleting from the 5' end of the DNA to create DNA comprising a sequence encoding a truncated enzyme as claimed in claim 2;

(3) culturing a host cell to containing a recombinant molecule comprising:

(a) the DNA encoding the truncated enzyme and (b) a promoter wherein said promoter and said DNA encoding the truncated enzyme are in such position and orientation with respect to each other that said DNA may be expressed in a host cell under control of said promoter; and (4) isolating the truncated enzyme from the host cell.

26. A vector containing the isolated nucleic acid molecule or DNA molecule as in any one of claims 1, 2, 3, 4, 5, 6, 7, 8, 9, 10, 11, 12 or 13.

27. The vector of claim 26 which is a plasmid.

28. In a method for sequencing DNA or labelling DNA wherein the improvement comprises using a *Bacillus stearothermophilus* DNA polymerase I enzyme from expression of the isolated DNA molecule as claimed in claim 3.

29. The method of claim 28 wherein in the isolated DNA molecule, nucleotides 1 to 1077 of FIG. 1 (SEQ ID NO: 1) are deleted.

30. The method of claim 28 wherein the isolated DNA molecule begins at nucleotide 1078 of FIG. 1 (SEQ ID NO: 1).

31. The method of claim 28 wherein in the isolated DNA molecule, nucleotides 1 to 1332 of FIG. 1 (SEQ ID NO: 1) are deleted.

32. The method of claim 28 wherein the isolated DNA molecule begins at nucleotide 1333 of FIG. 1 (SEQ ID NO: 1).

33. The method of claim 28 wherein in the isolated DNA molecule, nucleotides 1 to 1577 of FIG. 1 (SEQ ID NO: 1) are deleted.

34. The method of claim 28 wherein the isolated DNA molecule begins at nucleotide 1578 of FIG. 1 (SEQ ID NO: 1).

35. The method of claim 28 wherein in the isolated DNA molecule nucleotides 1 to 1815 of FIG. 1 (SEQ ID NO: 1) are deleted.

36. The method of claim 28 wherein the isolated DNA molecule begins at nucleotide 1816 of FIG. 1 (SEQ ID NO: 1).

37. The method of claim 28 wherein in the isolated DNA molecule nucleotides 1 to 2067 of FIG. 1 (SEQ ID NO: 1) are deleted.

38. The method of claim 28 wherein the isolated DNA molecule begins at nucleotide 2068 of FIG. 1 (SEQ ID NO: 1).

39. The method of claim 28 wherein the DNA polymerase enzyme begins at amino acid 286 of FIG. 1 (SEQ ID NO: 2).

40. The method of claim 28 wherein in the DNA polymerase enzyme, amino acids 1 to 370 of FIG. 1 (SEQ ID NO: 2) are deleted.

41. The method of claim 28 wherein the DNA polymerase enzyme begins at amino acid 371 of FIG. 1 (SEQ ID NO: 2).

42. The method of claim 28 wherein in the DNA polymerase enzyme, amino acids 1 to 452 of FIG. 1 (SEQ ID NO: 2) are deleted.

43. The method of claim 28 wherein the DNA polymerase enzyme begins at amino acid 453 of FIG. 1 (SEQ ID NO: 2).

44. The method of claim 28 wherein in the DNA polymerase enzyme, amino acids 1 to 531 of FIG. 1 (SEQ ID NO: 2) are deleted.

45. The method of claim 28 wherein the DNA polymerase enzyme begins at amino acid 532 of FIG. 1 (SEQ ID NO: 2).

46. The method of claim 28 wherein in the the DNA polymerase enzyme, amino acids 1 to 615 of FIG. 1 (SEQ ID NO: 2) are deleted.

47. The method of claim 28 wherein the DNA polymerase enzyme begins at amino acid 616 of FIG. 1 (SEQ ID NO: 2).

48. The method of claim 28 which is automated.
49. The method of claim 28 which is for DNA sequencing.
50. The method of claim 28 which is for DNA labelling.

* * * * *

UNITED STATES PATENT AND TRADEMARK OFFICE
CERTIFICATE OF CORRECTION

PATENT NO.    :  6,013,451

DATED         :  January 11, 2000

INVENTOR(s)   :  WONG ET AL.

It is certified that error appears in the above-identified patent and that said Letters Patent is hereby corrected as shown below:

ON THE COVER PAGE:

Item [30] FOREIGN APPLICATION PRIORITY DATA:

Delete: "Apr. 10, 1997    [SA]    Saudi Arabia    9701158"

insert Item --[30]    FOREIGN APPLICATION PRIORITY DATA:

Apr. 10, 1997    [SG]    Singapore    9701158--

Signed and Sealed this

Thirty-first Day of October, 2000

Attest:

Q. TODD DICKINSON

*Attesting Officer*    *Director of Patents and Trademarks*

SEQUENCE LISTING (1) GENERAL INFORMATION:

(iii) NUMBER OF SEQUENCES: 17

(2) INFORMATION FOR SEQ ID NO:1:

(i) SEQUENCE CHARACTERISTICS:
      (A) LENGTH: 2969 base pairs
      (B) TYPE: nucleic acid
      (C) STRANDEDNESS: single
      (D) TOPOLOGY: linear (ii) MOLECULE TYPE: DNA (genomic)

(xi) SEQUENCE DESCRIPTION: SEQ ID NO:1:

```
CAACACTACG TGGCGTCGAC AAGGCGCGCA GCCGCAACTC AGGCGGGACG GGCTGGGCCC      60

TTCGATCGTC AAGCACTTGG TCGAGGCGCA TCGCGGCTAC ATTACGGTGA CGAGCGAAGT     120

CGGGCGCGGC ACCGAGTTTA CGATTCATTT CCCGAAGCCG GAGCGGTAGC CGGCTTCTTT     180

TTATGGCCCC CGCCGGCGTG GTACAATAGA ACAAGGAACG TCCGAGGAGG GATGATGTTG     240

AAAAACAAGC TCGTCTTAAT TGACGGCAAC AGCGTGGCGT ACCGCGCCTT TTTTGCGTTG     300

CCGCTTTTGC ATAACGATAA AGGGATTCAT ACGAACGCAG TCTACGGGTT TACGATGATG     360

TTAAACAAAA TTTTGGCGGA AGAGCAGCCG ACCCACATTC TCGTTGCGTT TGACGCCGGG     420

AAAACGACGT TCCGCCATGA AACGTTCCAA GACTATAAAG GCGGGCGGCA GCAGACGCCG     480

CCGGAACTGT CGGAACAGTT TCCGCTCGTG CGCGAATTGC TCAAAGCGTA CCGCATCCCC     540

GCCTATGAGC TCGACCATTA TGAAGCGGAT GACATCATCG AACGATGGC GGCGCGGGCT      600

GAGCGAGAAG GGTTTGCAGT GAAAGTCATT TCCGGCGACC GCGATTTAAC CCAGCTTGCT     660

TCCCCGCAAG TGACGGTGGA GATTACGAAA AAAGGGATTA CCGACATCGA GTCGTACACG     720

CCGGAGACGG TCGTGGAAAA ATACGGCCTC ACCCCGGAGC AAATTGTCGA CTTGAAAGGA     780

TTGATGGGCG ACAAATCCGA CAACATCCCT GGCGTGCCCG GCATCGGGAA AAAACAGCC     840

GTCAAGCTGC TCAAGCAATT CGGCACGGTC GAAAACGTAC TGGCATCGAT CGATGAGATC     900

AAAGGGGAGA AGCTGAAAGA AAATTTGCGC CAATACCGGG ATTTGGCGCT TTTAAGCAAA     960

CAGCTGGCCG CTATTTGCCG CGACGCCCCG GTTGAGCTGA CGCTCGATGA CATTGTCTAC    1020

AAAGGAGAAG ACCGGGAAAA AGTGGTCGCC TTGTTTCAGG AGCTCGGATT CCAGTCGTTT    1080

CTCGACAAGA TGGCCGTCCA AACGGATGAA GGCGAAAAGC CGCTCGCCGG GATGGATTTT    1140

GCGATCGCCG ACAGCGTCAC GGACGAAATG CTCGCCGACA AAGCGGCCCT CGTCGTGGAG    1200

GTGGTGGGCG ACAACTATCA CCATGCCCCG ATTGTCGGGA TCGCCTTGGC CAACGAACGC    1260

GGGCGGTTTT TCCTGCGCCC GGAGACGGCC GTCGCCGATC CGAAATTTCT CGCTTGGCTT    1320

GGCGATGAGA CGAAGAAAAA AACGATGTTT GATTCAAAGC GGGCGGCCGT CGCGCTAAAT    1380

GGGAAAGGAA TCGAACTGGC TGGCGTCGGC GTCGTGTTCG ATCTGTTGCT GGCCGCTTAC    1440

TTGCTCGATC CGGCGCAGGC GGCGGGCGAC GTTGCCGCGG TGGCGAAAAT GCATCAGTAC    1500

GAGGCGGTGC GATCGGATGA GGCGGTCTAT GGAAAAGGAG CGAAGCGGAC GGTTCCTGAT    1560

GAACCGACGC TTGCCGAGCA GCTCGTCCGC AAGGCGGCGG CCATTTGGGC GCTTGAAGAG    1620

CCGTTGATGG ACGAACTGCG CCGCAACGAA CAAGATCGGC TGCTGACCGA GCTCGAACAC    1680

GCGCTGGCTG GCATTTTGGC CAATATGGAA TTTACTGGAG TGAAAGTGGA CACGAAGCGG    1740
```

-continued

```
CTTGAACAGA TGGGGCGGA GCTCACCGAG CAGCTGCAGG CGGTCGAGCG GCGCATTTAC    1800

GAACTCGCCG GCCAAGAGTT CAACATTAAC TCGCCGAAAC AGCTCGGGAC GGTTTTATTT    1860

GACAAGCTGC AGCTCCCGGT GTTGAAAAAG ACAAAAACCG GCTATTCGAC TTCAGCCGAT    1920

GTGCTAGAAA AGCTTGCACC GCACCATGAA ATCGTCGAAC ATATTTTGCA TTACCGCCAA    1980

CTCGGCAAGC TGCAGTCAAC GTATATTGAA GGGCTGCTGA AAGTGGTGCA CCCCGTGACG    2040

GGCAAAGTGC ACACGATGTT CAATCAGGCG TTGACGCAAA CCGGGCGCCT CAGCTCCGTC    2100

GAACCGAATT TGCAAAACAT TCCGATTCGG CTTGAGGAAG GGCGGAAAAT CCGCCAGGCG    2160

TTCGTGCCGT CGGAGCCGGA CTGGCTCATC TTTGCGGCCG ACTATTCGCA AATCGAGCTG    2220

CGCGTCCTCG CCCATATCGC GGAAGATGAC AATTTGATTG AAGCGTTCCG GCGCTGGTTG    2280

GACATCCATA CGAAAACAGC CATGGACATT TTCCATGTGA GCGAAGAAGA CGTGACAGCC    2340

AACATGCGCC GCCAAGCGAA GGCCGTCAAT TTTGGCATCG TGTACGGCAT TAGTGATTAC    2400

GGTCTGGCGC AAAACTTGAA CATTACGCGC AAAGAAGCGG CTGAATTTAT TGAGCGATAT    2460

TTTGCCAGTT TTCCAGGTGT AAAGCAATAT ATGGACAACA TTGTGCAAGA AGCGAAACAA    2520

AAAGGGTATG TGACGACGCT GCTGCATCGG CGCCGCTATT TGCCCGATAT TACAAGCCGC    2580

AACTTCAACG TCCGCACGTT CGCCGAGCGG ACGGCGATGA ACACACCGAT CCAGGGATCC    2640

GCTGCCGACA TCATTAAGAA AGCGATGATC GATCTAAGCG TGAGCGTGCG CGAAGAACGG    2700

CTGCAGGCGC GCCTGTTGCT GCAAGGTCAT GACGAACTCA TTTTGGAGGC GCCGAAAGAG    2760

GAAATCGGAC GGCTGTGCCG CCTCGTTCCG GAAGTGATGG AGCAAGCCGT GACACTTCGC    2820

GTGCCGCTGA AAGTCGATTA CCATTACGGT CCGACGTGGT ACGACGCCAA ATAAAAGCGG    2880

CCTGCCCGCA GCTGCTCGGT TTTTCACGGG GCCGACGACA ATGAGCTGTT GCTTTAAAAC    2940

AGGTGCACGA ACAGGAAAAG GAGGGAGGC                                      2969
```

(2) INFORMATION FOR SEQ ID NO:2:

(i) SEQUENCE CHARACTERISTICS:
        (A) LENGTH: 954 amino acids
        (B) TYPE: amino acid
        (C) STRANDEDNESS: single
        (D) TOPOLOGY: linear (ii) MOLECULE TYPE: amino acid (xi) SEQUENCE DESCRIPTION: SEQ ID NO:2:

```
Met Ala Ser Thr Arg Arg Ala Ala Ala Thr Gln Ala Gly Arg Ala Gly
 1               5                  10                  15

Pro Phe Asp Arg Gln Ala Leu Gly Arg Gly Ala Ser Arg Leu His Tyr
                20                  25                  30

Gly Asp Glu Arg Ser Arg Ala Arg His Arg Val Tyr Asp Ser Phe Pro
            35                  40                  45

Glu Ala Gly Ala Val Ala Gly Phe Phe Leu Trp Pro Pro Ala Trp
        50                  55                  60

Tyr Asn Arg Thr Arg Asn Val Arg Gly Gly Met Met Leu Lys Asn Lys
65                  70                  75                  80

Leu Val Leu Ile Asp Gly Asn Ser Val Ala Tyr Arg Ala Phe Phe Ala
                85                  90                  95

Leu Pro Leu Leu His Asn Asp Lys Gly Ile His Thr Asn Ala Val Tyr
                100                 105                 110

Gly Phe Thr Met Met Leu Asn Lys Ile Leu Ala Glu Glu Gln Pro Thr
            115                 120                 125

His Ile Leu Val Ala Phe Asp Ala Gly Lys Thr Thr Phe Arg His Glu
```

-continued

```
                130                 135                 140
Thr Phe Gln Asp Tyr Lys Gly Gly Arg Gln Gln Thr Pro Pro Glu Leu
145                 150                 155                 160

Ser Glu Gln Phe Pro Leu Val Arg Glu Leu Leu Lys Ala Tyr Arg Ile
                165                 170                 175

Pro Ala Tyr Glu Leu Asp His Tyr Glu Ala Asp Asp Ile Ile Gly Thr
            180                 185                 190

Met Ala Ala Arg Ala Glu Arg Glu Gly Phe Ala Val Lys Val Ile Ser
            195                 200                 205

Gly Asp Arg Asp Leu Thr Gln Leu Ala Ser Pro Gln Val Thr Val Glu
210                 215                 220

Ile Thr Lys Lys Gly Ile Thr Asp Ile Glu Ser Tyr Thr Pro Glu Thr
225                 230                 235                 240

Val Val Glu Lys Tyr Gly Leu Thr Pro Glu Gln Ile Val Asp Leu Lys
                245                 250                 255

Gly Leu Met Gly Asp Lys Ser Asp Asn Ile Pro Gly Val Pro Gly Ile
            260                 265                 270

Gly Lys Lys Thr Ala Val Lys Leu Leu Lys Gln Phe Gly Thr Val Glu
            275                 280                 285

Asn Val Leu Ala Ser Ile Asp Glu Ile Lys Gly Glu Lys Leu Lys Glu
290                 295                 300

Asn Leu Arg Gln Tyr Arg Asp Leu Ala Leu Leu Ser Lys Gln Leu Ala
305                 310                 315                 320

Ala Ile Cys Arg Asp Ala Pro Val Glu Leu Thr Leu Asp Asp Ile Val
                325                 330                 335

Tyr Lys Gly Glu Asp Arg Glu Lys Val Val Ala Leu Phe Gln Glu Leu
            340                 345                 350

Gly Phe Gln Ser Phe Leu Asp Lys Met Ala Val Gln Thr Asp Glu Gly
            355                 360                 365

Glu Lys Pro Leu Ala Gly Met Asp Phe Ala Ile Ala Asp Ser Val Thr
370                 375                 380

Asp Glu Met Leu Ala Asp Lys Ala Ala Leu Val Val Glu Val Val Gly
385                 390                 395                 400

Asp Asn Tyr His His Ala Pro Ile Val Gly Ile Ala Leu Ala Asn Glu
                405                 410                 415

Arg Gly Arg Phe Phe Leu Arg Pro Glu Thr Ala Val Ala Asp Pro Lys
            420                 425                 430

Phe Leu Ala Trp Leu Gly Asp Glu Thr Lys Lys Lys Thr Met Phe Asp
            435                 440                 445

Ser Lys Arg Ala Ala Val Ala Leu Asn Gly Lys Gly Ile Glu Leu Ala
450                 455                 460

Gly Val Gly Val Val Phe Asp Leu Leu Leu Ala Ala Tyr Leu Leu Asp
465                 470                 475                 480

Pro Ala Gln Ala Ala Gly Asp Val Ala Ala Val Ala Lys Met His Gln
                485                 490                 495

Tyr Glu Ala Val Arg Ser Asp Glu Ala Val Tyr Gly Lys Gly Ala Lys
            500                 505                 510

Arg Thr Val Pro Asp Glu Pro Thr Leu Ala Glu Gln Leu Val Arg Lys
            515                 520                 525

Ala Ala Ala Ile Trp Ala Leu Glu Glu Pro Leu Met Asp Glu Leu Arg
530                 535                 540

Arg Asn Glu Gln Asp Arg Leu Leu Thr Glu Leu Glu His Ala Leu Ala
545                 550                 555                 560
```

```
Gly Ile Leu Ala Asn Met Glu Phe Thr Gly Val Lys Val Asp Thr Lys
                565                 570                 575
Arg Leu Glu Gln Met Gly Ala Glu Leu Thr Glu Gln Leu Gln Ala Val
            580                 585                 590
Glu Arg Arg Ile Tyr Glu Leu Ala Gly Gln Glu Phe Asn Ile Asn Ser
        595                 600                 605
Pro Lys Gln Leu Gly Thr Val Leu Phe Asp Lys Leu Gln Leu Pro Val
    610                 615                 620
Leu Lys Lys Thr Lys Thr Gly Tyr Ser Thr Ser Ala Asp Val Leu Glu
625                 630                 635                 640
Lys Leu Ala Pro His His Glu Ile Val Glu His Ile Leu His Tyr Arg
                645                 650                 655
Gln Leu Gly Lys Leu Gln Ser Thr Tyr Ile Glu Gly Leu Leu Lys Val
            660                 665                 670
Val His Pro Val Thr Gly Lys Val His Thr Met Phe Asn Gln Ala Leu
        675                 680                 685
Thr Gln Thr Gly Arg Leu Ser Ser Val Glu Pro Asn Leu Gln Asn Ile
    690                 695                 700
Pro Ile Arg Leu Glu Glu Gly Arg Lys Ile Arg Gln Ala Phe Val Pro
705                 710                 715                 720
Ser Glu Pro Asp Trp Leu Ile Phe Ala Ala Asp Tyr Ser Gln Ile Glu
                725                 730                 735
Leu Arg Val Leu Ala His Ile Ala Glu Asp Asp Asn Leu Ile Glu Ala
            740                 745                 750
Phe Arg Arg Trp Leu Asp Ile His Thr Lys Thr Ala Met Asp Ile Phe
        755                 760                 765
His Val Ser Glu Glu Asp Val Thr Ala Asn Met Arg Arg Gln Ala Lys
    770                 775                 780
Ala Val Asn Phe Gly Ile Val Tyr Gly Ile Ser Asp Tyr Gly Leu Ala
785                 790                 795                 800
Gln Asn Leu Asn Ile Thr Arg Lys Glu Ala Ala Glu Phe Ile Glu Arg
                805                 810                 815
Tyr Phe Ala Ser Phe Pro Gly Val Lys Gln Tyr Met Asp Asn Ile Val
            820                 825                 830
Gln Glu Ala Lys Gln Lys Gly Tyr Val Thr Thr Leu Leu His Arg Arg
        835                 840                 845
Arg Tyr Leu Pro Asp Ile Thr Ser Arg Asn Phe Asn Val Arg Thr Phe
    850                 855                 860
Ala Glu Arg Thr Ala Met Asn Thr Pro Ile Gln Gly Ser Ala Ala Asp
865                 870                 875                 880
Ile Ile Lys Lys Ala Met Ile Asp Leu Ser Val Ser Val Arg Glu Glu
                885                 890                 895
Arg Leu Gln Ala Arg Leu Leu Leu Gln Gly His Asp Glu Leu Ile Leu
            900                 905                 910
Glu Ala Pro Lys Glu Glu Ile Gly Arg Leu Cys Arg Leu Val Pro Glu
        915                 920                 925
Val Met Glu Gln Ala Val Thr Leu Arg Val Pro Leu Lys Val Asp Tyr
    930                 935                 940
His Tyr Gly Pro Thr Trp Tyr Asp Ala Lys
945                 950
```

(2) INFORMATION FOR SEQ ID NO:3:

(i) SEQUENCE CHARACTERISTICS:
        (A) LENGTH: 624 amino acids (B) TYPE: amino acid
(C) STRANDEDNESS: single
(D) TOPOLOGY: linear (ii) MOLECULE TYPE: amino acid (xi) SEQUENCE DESCRIPTION: SEQ ID NO:3:

```
Met Ala Val Gln Thr Asp Glu Gly Glu Lys Pro Leu Ala Gly Met Asp
1               5                   10                  15

Phe Ala Ile Ala Asp Ser Val Thr Asp Glu Met Leu Ala Asp Lys Ala
            20                  25                  30

Ala Leu Val Val Glu Val Val Gly Asp Asn Tyr His His Ala Pro Ile
        35                  40                  45

Val Gly Ile Ala Leu Ala Asn Glu Arg Gly Arg Phe Phe Leu Arg Pro
50                  55                  60

Glu Thr Ala Val Ala Asp Pro Lys Phe Leu Ala Trp Leu Gly Asp Glu
65                  70                  75                  80

Thr Lys Lys Lys Thr Met Phe Asp Ser Lys Arg Ala Ala Val Ala Leu
                85                  90                  95

Asn Gly Lys Gly Ile Glu Leu Ala Gly Val Gly Val Val Phe Asp Leu
            100                 105                 110

Leu Leu Ala Ala Tyr Leu Leu Asp Pro Ala Gln Ala Ala Gly Asp Val
        115                 120                 125

Ala Ala Val Ala Lys Met His Gln Tyr Glu Ala Val Arg Ser Asp Glu
130                 135                 140

Ala Val Tyr Gly Lys Gly Ala Lys Arg Thr Val Pro Asp Glu Pro Thr
145                 150                 155                 160

Leu Ala Glu Gln Leu Val Arg Lys Ala Ala Ile Trp Ala Leu Glu
                165                 170                 175

Glu Pro Leu Met Asp Glu Leu Arg Arg Asn Glu Gln Asp Arg Leu Leu
            180                 185                 190

Thr Glu Leu Glu His Ala Leu Ala Gly Ile Leu Ala Asn Met Glu Phe
        195                 200                 205

Thr Gly Val Lys Val Asp Thr Lys Arg Leu Glu Gln Met Gly Ala Glu
210                 215                 220

Leu Thr Glu Gln Leu Gln Ala Val Glu Arg Arg Ile Tyr Glu Leu Ala
225                 230                 235                 240

Gly Gln Glu Phe Asn Ile Asn Ser Pro Lys Gln Leu Gly Thr Val Leu
                245                 250                 255

Phe Asp Lys Leu Gln Leu Pro Val Leu Lys Lys Thr Lys Thr Gly Tyr
            260                 265                 270

Ser Thr Ser Ala Asp Val Leu Glu Lys Leu Ala Pro His His Glu Ile
        275                 280                 285

Val Glu His Ile Leu His Tyr Arg Gln Leu Gly Lys Leu Gln Ser Thr
290                 295                 300

Tyr Ile Glu Gly Leu Leu Lys Val Val His Pro Val Thr Gly Lys Val
305                 310                 315                 320

His Thr Met Phe Asn Gln Ala Leu Thr Gln Thr Gly Arg Leu Ser Ser
                325                 330                 335

Val Glu Pro Asn Leu Gln Asn Ile Pro Ile Arg Leu Glu Glu Gly Arg
            340                 345                 350

Lys Ile Arg Gln Ala Phe Val Pro Ser Glu Pro Asp Trp Leu Ile Phe
        355                 360                 365

Ala Ala Asp Tyr Ser Gln Ile Glu Leu Arg Val Leu Ala His Ile Ala
370                 375                 380
```

-continued

```
Glu Asp Asp Asn Leu Ile Glu Ala Phe Arg Arg Trp Leu Asp Ile His
385                 390                 395                 400

Thr Lys Thr Ala Met Asp Ile Phe His Val Ser Glu Glu Asp Val Thr
                405                 410                 415

Ala Asn Met Arg Arg Gln Ala Lys Ala Val Asn Phe Gly Ile Val Tyr
            420                 425                 430

Gly Ile Ser Asp Tyr Gly Leu Ala Gln Asn Leu Asn Ile Thr Arg Lys
        435                 440                 445

Glu Ala Ala Glu Phe Ile Glu Arg Tyr Phe Ala Ser Phe Pro Gly Val
    450                 455                 460

Lys Gln Tyr Met Asp Asn Ile Val Gln Glu Ala Lys Gln Lys Gly Tyr
465                 470                 475                 480

Val Thr Thr Leu Leu His Arg Arg Tyr Leu Pro Asp Ile Thr Ser
                485                 490                 495

Arg Asn Phe Asn Val Arg Thr Phe Ala Glu Arg Thr Ala Met Asn Thr
                500                 505                 510

Pro Ile Gln Gly Ser Ala Ala Asp Ile Ile Lys Lys Ala Met Ile Asp
            515                 520                 525

Leu Ser Val Ser Val Arg Glu Glu Arg Leu Gln Ala Arg Leu Leu Leu
530                 535                 540

Gln Gly His Asp Glu Leu Ile Leu Glu Ala Pro Lys Glu Glu Ile Gly
545                 550                 555                 560

Arg Leu Cys Arg Leu Val Pro Glu Val Met Glu Gln Ala Val Thr Leu
                565                 570                 575

Arg Val Pro Leu Lys Val Asp Tyr His Tyr Gly Pro Thr Trp Tyr Asp
                580                 585                 590

Ala Lys Lys Arg Pro Ala Arg Ser Cys Ser Val Phe His Gly Ala Asp
            595                 600                 605

Asp Asn Glu Leu Leu Leu Asn Arg Cys Thr Asn Arg Lys Arg Arg Glu
610                 615                 620
```

(2) INFORMATION FOR SEQ ID NO:4:

(i) SEQUENCE CHARACTERISTICS:
        (A) LENGTH: 539 amino acids
        (B) TYPE: amino acid
        (C) STRANDEDNESS: single
        (D) TOPOLOGY: linear (ii) MOLECULE TYPE: amino acid (xi) SEQUENCE DESCRIPTION: SEQ ID NO:4:

```
Met Val Asp Ser Lys Arg Ala Ala Val Ala Leu Asn Gly Lys Gly Ile
1               5                   10                  15

Glu Leu Ala Gly Val Gly Val Val Phe Asp Leu Leu Leu Ala Ala Tyr
            20                  25                  30

Leu Leu Asp Pro Ala Gln Ala Ala Gly Asp Val Ala Ala Val Ala Lys
        35                  40                  45

Met His Gln Tyr Glu Ala Val Arg Ser Asp Glu Ala Val Tyr Gly Lys
    50                  55                  60

Gly Ala Lys Arg Thr Val Pro Asp Glu Pro Thr Leu Ala Glu Gln Leu
65                  70                  75                  80

Val Arg Lys Ala Ala Ile Trp Ala Leu Glu Glu Pro Leu Met Asp
                85                  90                  95

Glu Leu Arg Arg Asn Glu Gln Asp Arg Leu Leu Thr Glu Leu Glu His
                100                 105                 110

Ala Leu Ala Gly Ile Leu Ala Asn Met Glu Phe Thr Gly Val Lys Val
```

```
                115                 120                 125
Asp Thr Lys Arg Leu Glu Gln Met Gly Ala Glu Leu Thr Glu Gln Leu
    130                 135                 140
Gln Ala Val Glu Arg Arg Ile Tyr Glu Leu Ala Gly Gln Glu Phe Asn
145                 150                 155                 160
Ile Asn Ser Pro Lys Gln Leu Gly Thr Val Leu Phe Asp Lys Leu Gln
                165                 170                 175
Leu Pro Val Leu Lys Thr Lys Thr Gly Tyr Ser Thr Ser Ala Asp
                180                 185                 190
Val Leu Glu Lys Leu Ala Pro His His Glu Ile Val Glu His Ile Leu
            195                 200                 205
His Tyr Arg Gln Leu Gly Lys Leu Gln Ser Thr Tyr Ile Glu Gly Leu
    210                 215                 220
Leu Lys Val Val His Pro Val Thr Gly Lys Val His Thr Met Phe Asn
225                 230                 235                 240
Gln Ala Leu Thr Gln Thr Gly Arg Leu Ser Ser Val Glu Pro Asn Leu
                245                 250                 255
Gln Asn Ile Pro Ile Arg Leu Glu Glu Gly Arg Lys Ile Arg Gln Ala
                260                 265                 270
Phe Val Pro Ser Glu Pro Asp Trp Leu Ile Phe Ala Ala Asp Tyr Ser
                275                 280                 285
Gln Ile Glu Leu Arg Val Leu Ala His Ile Ala Glu Asp Asp Asn Leu
    290                 295                 300
Ile Glu Ala Phe Arg Arg Trp Leu Asp Ile His Thr Lys Thr Ala Met
305                 310                 315                 320
Asp Ile Phe His Val Ser Glu Glu Asp Val Thr Ala Asn Met Arg Arg
                325                 330                 335
Gln Ala Lys Ala Val Asn Phe Gly Ile Val Tyr Gly Ile Ser Asp Tyr
                340                 345                 350
Gly Leu Ala Gln Asn Leu Asn Ile Thr Arg Lys Glu Ala Ala Glu Phe
            355                 360                 365
Ile Glu Arg Tyr Phe Ala Ser Phe Pro Gly Val Lys Gln Tyr Met Asp
    370                 375                 380
Asn Ile Val Gln Glu Ala Lys Gln Lys Gly Tyr Val Thr Thr Leu Leu
385                 390                 395                 400
His Arg Arg Arg Tyr Leu Pro Asp Ile Thr Ser Arg Asn Phe Asn Val
                405                 410                 415
Arg Thr Phe Ala Glu Arg Thr Ala Met Asn Thr Pro Ile Gln Gly Ser
                420                 425                 430
Ala Ala Asp Ile Ile Lys Lys Ala Met Ile Asp Leu Ser Val Ser Val
            435                 440                 445
Arg Glu Glu Arg Leu Gln Ala Arg Leu Leu Leu Gln Gly His Asp Glu
    450                 455                 460
Leu Ile Leu Glu Ala Pro Lys Glu Glu Ile Gly Arg Leu Cys Arg Leu
465                 470                 475                 480
Val Pro Glu Val Met Glu Gln Ala Val Thr Leu Arg Val Pro Leu Lys
                485                 490                 495
Val Asp Tyr His Tyr Gly Pro Thr Trp Tyr Asp Ala Lys Lys Arg Pro
                500                 505                 510
Ala Arg Ser Cys Ser Val Phe His Gly Ala Asp Asp Asn Glu Leu Leu
            515                 520                 525
Leu Asn Arg Cys Thr Asn Arg Lys Arg Glu
    530                 535
```

(2) INFORMATION FOR SEQ ID NO:5:

(i) SEQUENCE CHARACTERISTICS:
        (A) LENGTH: 457 amino acids
        (B) TYPE: amino acid
        (C) STRANDEDNESS: single
        (D) TOPOLOGY: linear (ii) MOLECULE TYPE: amino acid (xi) SEQUENCE DESCRIPTION: SEQ ID NO:5:

```
Met Ala Ala Ala Ile Trp Ala Leu Glu Glu Pro Leu Met Asp Glu Leu
 1               5                  10                  15

Arg Arg Asn Glu Gln Asp Arg Leu Leu Thr Glu Leu Glu His Ala Leu
            20                  25                  30

Ala Gly Ile Leu Ala Asn Met Glu Phe Thr Gly Val Lys Val Asp Thr
        35                  40                  45

Lys Arg Leu Glu Gln Met Gly Ala Glu Leu Thr Glu Gln Leu Gln Ala
50                  55                  60

Val Glu Arg Arg Ile Tyr Glu Leu Ala Gly Gln Glu Phe Asn Ile Asn
65                  70                  75                  80

Ser Pro Lys Gln Leu Gly Thr Val Leu Phe Asp Lys Leu Gln Leu Pro
                85                  90                  95

Val Leu Lys Lys Thr Lys Thr Gly Tyr Ser Thr Ser Ala Asp Val Leu
            100                 105                 110

Glu Lys Leu Ala Pro His His Glu Ile Val Glu His Ile Leu His Tyr
        115                 120                 125

Arg Gln Leu Gly Lys Leu Gln Ser Thr Tyr Ile Glu Gly Leu Leu Lys
130                 135                 140

Val Val His Pro Val Thr Gly Lys Val His Thr Met Phe Asn Gln Ala
145                 150                 155                 160

Leu Thr Gln Thr Gly Arg Leu Ser Ser Val Glu Pro Asn Leu Gln Asn
                165                 170                 175

Ile Pro Ile Arg Leu Glu Glu Gly Arg Lys Ile Arg Gln Ala Phe Val
            180                 185                 190

Pro Ser Glu Pro Asp Trp Leu Ile Phe Ala Ala Asp Tyr Ser Gln Ile
        195                 200                 205

Glu Leu Arg Val Leu Ala His Ile Ala Glu Asp Asp Asn Leu Ile Glu
210                 215                 220

Ala Phe Arg Arg Trp Leu Asp Ile His Thr Lys Thr Ala Met Asp Ile
225                 230                 235                 240

Phe His Val Ser Glu Glu Asp Val Thr Ala Asn Met Arg Arg Gln Ala
                245                 250                 255

Lys Ala Val Asn Phe Gly Ile Val Tyr Gly Ile Ser Asp Tyr Gly Leu
            260                 265                 270

Ala Gln Asn Leu Asn Ile Thr Arg Lys Glu Ala Ala Glu Phe Ile Glu
        275                 280                 285

Arg Tyr Phe Ala Ser Phe Pro Gly Val Lys Gln Tyr Met Asp Asn Ile
290                 295                 300

Val Gln Glu Ala Lys Gln Lys Gly Tyr Val Thr Thr Leu Leu His Arg
305                 310                 315                 320

Arg Arg Tyr Leu Pro Asp Ile Thr Ser Arg Asn Phe Asn Val Arg Thr
                325                 330                 335

Phe Ala Glu Arg Thr Ala Met Asn Thr Pro Ile Gln Gly Ser Ala Ala
            340                 345                 350

Asp Ile Ile Lys Lys Ala Met Ile Asp Leu Ser Val Ser Val Arg Glu
```

```
                355                 360                 365
Glu Arg Leu Gln Ala Arg Leu Leu Gln Gly His Asp Glu Leu Ile
    370                 375                 380

Leu Glu Ala Pro Lys Glu Ile Gly Arg Leu Cys Arg Leu Val Pro
385                 390                 395                 400

Glu Val Met Glu Gln Ala Val Thr Leu Arg Val Pro Leu Lys Val Asp
                405                 410                 415

Tyr His Tyr Gly Pro Thr Trp Tyr Asp Ala Lys Lys Arg Pro Ala Arg
                420                 425                 430

Ser Cys Ser Val Phe His Gly Ala Asp Asp Asn Glu Leu Leu Leu Asn
                435                 440                 445

Arg Cys Thr Asn Arg Lys Arg Arg Glu
450                 455
```

(2) INFORMATION FOR SEQ ID NO:6:

(i) SEQUENCE CHARACTERISTICS:
        (A) LENGTH: 378 amino acids
        (B) TYPE: amino acid
        (C) STRANDEDNESS: single
        (D) TOPOLOGY: linear (ii) MOLECULE TYPE: amino acid (xi) SEQUENCE DESCRIPTION: SEQ ID NO:6:

```
Met Ala Pro Lys Gln Leu Gly Thr Val Leu Phe Asp Lys Leu Gln Leu
1               5                   10                  15

Pro Val Leu Lys Lys Thr Lys Thr Gly Tyr Ser Thr Ser Ala Asp Val
                20                  25                  30

Leu Glu Lys Leu Ala Pro His His Glu Ile Val Glu His Ile Leu His
            35                  40                  45

Tyr Arg Gln Leu Gly Lys Leu Gln Ser Thr Tyr Ile Glu Gly Leu Leu
    50                  55                  60

Lys Val Val His Pro Val Thr Gly Lys Val His Thr Met Phe Asn Gln
65                  70                  75                  80

Ala Leu Thr Gln Thr Gly Arg Leu Ser Ser Val Glu Pro Asn Leu Gln
                85                  90                  95

Asn Ile Pro Ile Arg Leu Glu Glu Gly Arg Lys Ile Arg Gln Ala Phe
            100                 105                 110

Val Pro Ser Glu Pro Asp Trp Leu Ile Phe Ala Ala Asp Tyr Ser Gln
        115                 120                 125

Ile Glu Leu Arg Val Leu Ala His Ile Ala Glu Asp Asp Asn Leu Ile
    130                 135                 140

Glu Ala Phe Arg Arg Trp Leu Asp Ile His Thr Lys Thr Ala Met Asp
145                 150                 155                 160

Ile Phe His Val Ser Glu Glu Asp Val Thr Ala Asn Met Arg Arg Gln
                165                 170                 175

Ala Lys Ala Val Asn Phe Gly Ile Val Tyr Gly Ile Ser Asp Tyr Gly
            180                 185                 190

Leu Ala Gln Asn Leu Asn Ile Thr Arg Lys Glu Ala Ala Glu Phe Ile
        195                 200                 205

Glu Arg Tyr Phe Ala Ser Phe Pro Gly Val Lys Gln Tyr Met Asp Asn
    210                 215                 220

Ile Val Gln Glu Ala Lys Gln Lys Gly Tyr Val Thr Thr Leu Leu His
225                 230                 235                 240

Arg Arg Arg Tyr Leu Pro Asp Ile Thr Ser Arg Asn Phe Asn Val Arg
                245                 250                 255
```

-continued

```
Thr Phe Ala Glu Arg Thr Ala Met Asn Thr Pro Ile Gln Gly Ser Ala
            260                 265                 270

Ala Asp Ile Ile Lys Lys Ala Met Ile Asp Leu Ser Val Ser Val Arg
        275                 280                 285

Glu Glu Arg Leu Gln Ala Arg Leu Leu Leu Gln Gly His Asp Glu Leu
    290                 295                 300

Ile Leu Glu Ala Pro Lys Glu Glu Ile Gly Arg Leu Cys Arg Leu Val
305                 310                 315                 320

Pro Glu Val Met Glu Gln Ala Val Thr Leu Arg Val Pro Leu Lys Val
                325                 330                 335

Asp Tyr His Tyr Gly Pro Thr Trp Tyr Asp Ala Lys Lys Arg Pro Ala
            340                 345                 350

Arg Ser Cys Ser Val Phe His Gly Ala Asp Asp Asn Glu Leu Leu Leu
        355                 360                 365

Asn Arg Cys Thr Asn Arg Lys Arg Glu
    370                 375
```

(2) INFORMATION FOR SEQ ID NO:7:

(i) SEQUENCE CHARACTERISTICS:
    (A) LENGTH: 294 amino acids
    (B) TYPE: amino acid
    (C) STRANDEDNESS: single
    (D) TOPOLOGY: linear (ii) MOLECULE TYPE: amino acid (xi) SEQUENCE DESCRIPTION: SEQ ID NO:7:

```
Met Gly Arg Leu Ser Ser Val Glu Pro Asn Leu Gln Asn Ile Pro Ile
1               5                   10                  15

Arg Leu Glu Glu Gly Arg Lys Ile Arg Gln Ala Phe Val Pro Ser Glu
            20                  25                  30

Pro Asp Trp Leu Ile Phe Ala Ala Asp Tyr Ser Gln Ile Glu Leu Arg
        35                  40                  45

Val Leu Ala His Ile Ala Glu Asp Asp Asn Leu Ile Glu Ala Phe Arg
    50                  55                  60

Arg Trp Leu Asp Ile His Thr Lys Thr Ala Met Asp Ile Phe His Val
65                  70                  75                  80

Ser Glu Glu Asp Val Thr Ala Asn Met Arg Arg Gln Ala Lys Ala Val
                85                  90                  95

Asn Phe Gly Ile Val Tyr Gly Ile Ser Asp Tyr Gly Leu Ala Gln Asn
            100                 105                 110

Leu Asn Ile Thr Arg Lys Glu Ala Ala Glu Phe Ile Glu Arg Tyr Phe
        115                 120                 125

Ala Ser Phe Pro Gly Val Lys Gln Tyr Met Asp Asn Ile Val Gln Glu
    130                 135                 140

Ala Lys Gln Lys Gly Tyr Val Thr Thr Leu Leu His Arg Arg Arg Tyr
145                 150                 155                 160

Leu Pro Asp Ile Thr Ser Arg Asn Phe Asn Val Arg Thr Phe Ala Glu
                165                 170                 175

Arg Thr Ala Met Asn Thr Pro Ile Gln Gly Ser Ala Ala Asp Ile Ile
            180                 185                 190

Lys Lys Ala Met Ile Asp Leu Ser Val Ser Val Arg Glu Glu Arg Leu
        195                 200                 205

Gln Ala Arg Leu Leu Leu Gln Gly His Asp Glu Leu Ile Leu Glu Ala
    210                 215                 220
```

```
Pro Lys Glu Glu Ile Gly Arg Leu Cys Arg Leu Val Pro Val Met
225                 230                 235                 240

Glu Gln Ala Val Thr Leu Arg Val Pro Leu Lys Val Asp Tyr His Tyr
            245                 250                 255

Gly Pro Thr Trp Tyr Asp Ala Lys Lys Arg Pro Ala Arg Ser Cys Ser
                260                 265                 270

Val Phe His Gly Ala Asp Asp Asn Glu Leu Leu Leu Asn Arg Cys Thr
        275                 280                 285

Asn Arg Lys Arg Arg Glu
    290
```

(2) INFORMATION FOR SEQ ID NO:8:

(i) SEQUENCE CHARACTERISTICS:
        (A) LENGTH: 1880 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:8:

```
ATGGCCGTCC AAACGGATGA AGGCGAAAAG CCGCTCGCCG GGATGGATTT TGCGATCGCC    60

GACAGCGTCA CGGACGAAAT GCTCGCCGAC AAAGCGGCCC TCGTCGTGGA GGTGGTGGGC   120

GACAACTATC ACCATGCCCC GATTGTCGGG ATCGCCTTGG CCAACGAACG CGGGCGGTTT   180

TTCCTGCGCC CGGAGACGGC CGTCGCCGAT CCGAAATTTC TCGCTTGGCT TGGCGATGAG   240

ACGAAGAAAA AAACGATGTT TGATTCAAAG CGGGCGGCCG TCGCGCTAAA TGGGAAAGGA   300

ATCGAACTGG CTGGCGTCGG CGTCGTGTTC GATCTGTTGC TGGCCGCTTA CTTGCTCGAT   360

CCGGCGCAGG CGGCGGGCGA CGTTGCCGCG GTGGCGAAAA TGCATCAGTA CGAGGCGGTG   420

CGATCGGATG AGGCGGTCTA TGGAAAAGGA GCGAAGCGGA CGGTTCCTGA TGAACCGACG   480

CTTGCCGAGC AGCTCGTCCG CAAGGCGGCG GCCATTTGGG CGCTTGAAGA GCCGTTGATG   540

GACGAACTGC GCCGCAACGA ACAAGATCGG CTGCTGACCG AGCTCGAACA CGCGCTGGCT   600

GGCATTTTGG CCAATATGGA ATTTACTGGA GTGAAAGTGG ACACGAAGCG GCTTGAACAG   660

ATGGGGGCGG AGCTCACCGA GCAGCTGCAG GCGGTCGAGC GGCGCATTTA CGAACTCGCC   720

GGCCAAGAGT TCAACATTAA CTCGCCGAAA CAGCTCGGGA CGGTTTTATT TGACAAGCTG   780

CAGCTCCCGG TGTTGAAAAA GACAAAAACC GGCTATTCGA CTTCAGCCGA TGTGCTAGAA   840

AAGCTTGCAC CGCACCATGA AATCGTCGAA CATATTTTGC ATTACCGCCA ACTCGGCAAG   900

CTGCAGTCAA CGTATATTGA AGGGCTGCTG AAAGTGGTGC ACCCCGTGAC GGGCAAAGTG   960

CACACGATGT TCAATCAGGC GTTGACGCAA ACCGGGCGCC TCAGCTCCGT CGAACCGAAT  1020

TTGCAAAACA TTCCGATTCG GCTTGAGGAA GGGCGGAAAA TCCGCCAGGC GTTCGTGCCG  1080

TCGGAGCCGG ACTGGCTCAT CTTTGCGGCC GACTATTCGC AAATCGAGCT GCGCGTCCTC  1140

GCCCATATCG CGGAAGATGA CAATTTGATT GAAGCGTTCC GGCGCTGGTT GGACATCCAT  1200

ACGAAAACAG CCATGGACAT TTTCCATGTG AGCGAAGAAG ACGTGACAGC CAACATGCGC  1260

CGCCAAGCGA AGGCCGTCAA TTTTGGCATC GTGTACGGCA TTAGTGATTA CGGTCTGGCG  1320

CAAAACTTGA ACATTACGCG CAAAGAAGCG GCTGAATTTA TTGAGCGATA TTTTGCCAGT  1380

TTTCCAGGTG TAAAGCAATA TATGGACAAC ATTGTGCAAG AAGCGAAACA AAAAGGGTAT  1440

GTGACGACGC TGCTGCATCG GCGCCGCTAT TTGCCCGATA TTACAAGCCG CAACTTCAAC  1500

GTCCGCACGT TCGCCGAGCG GACGGCGATG AACACACCGA TCCAGGGATC CGCTGCCGAC  1560
```

-continued

| ATCATTAAGA | AAGCGATGAT | CGATCTAAGC | GTGAGCGTGC | GCGAAGAACG | GCTGCAGGCG | 1620 |
| CGCCTGTTGC | TGCAAGGTCA | TGACGAACTC | ATTTTGGAGG | CGCCGAAAGA | GGAAATCGGA | 1680 |
| CGGCTGTGCC | GCCTCGTTCC | GGAAGTGATG | GAGCAAGCCG | TGACACTTCG | CGTGCCGCTG | 1740 |
| AAAGTCGATT | ACCATTACGG | TCCGACGTGG | TACGACGCCA | AATAAAAGCG | GCCTGCCCGC | 1800 |
| AGCTGCTCGG | TTTTTCACGG | GGCCGACGAC | AATGAGCTGT | TGCTTTAAAA | CAGGTGCACG | 1860 |
| AACAGGAAAA | GGAGGGAGGC | | | | | 1880 |

(2) INFORMATION FOR SEQ ID NO:9:

(i) SEQUENCE CHARACTERISTICS:
        (A) LENGTH: 1625 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:9:

| ATGGTTGATT | CAAAGCGGGC | GGCCGTCGCG | CTAAATGGGA | AAGGAATCGA | ACTGGCTGGC | 60 |
| GTCGGCGTCG | TGTTCGATCT | GTTGCTGGCC | GCTTACTTGC | TCGATCCGGC | GCAGGCGGCG | 120 |
| GGCGACGTTG | CCGCGGTGGC | GAAAATGCAT | CAGTACGAGG | CGGTGCGATC | GGATGAGGCG | 180 |
| GTCTATGGAA | AAGGAGCGAA | GCGGACGGTT | CCTGATGAAC | CGACGCTTGC | CGAGCAGCTC | 240 |
| GTCCGCAAGG | CGGCGGCCAT | TTGGGCGCTT | GAAGAGCCGT | TGATGGACGA | ACTGCGCCGC | 300 |
| AACGAACAAG | ATCGGCTGCT | GACCGAGCTC | GAACACGCGC | TGGCTGGCAT | TTTGGCCAAT | 360 |
| ATGGAATTTA | CTGGAGTGAA | AGTGGACACG | AAGCGGCTTG | AACAGATGGG | GGCGGAGCTC | 420 |
| ACCGAGCAGC | TGCAGGCGGT | CGAGCGGCGC | ATTTACGAAC | TCGCCGGCCA | AGAGTTCAAC | 480 |
| ATTAACTCGC | CGAAACAGCT | CGGGACGGTT | TTATTTGACA | AGCTGCAGCT | CCCGGTGTTG | 540 |
| AAAAAGACAA | AAACCGGCTA | TTCGACTTCA | GCCGATGTGC | TAGAAAAGCT | TGCACCGCAC | 600 |
| CATGAAATCG | TCGAACATAT | TTTGCATTAC | CGCCAACTCG | GCAAGCTGCA | GTCAACGTAT | 660 |
| ATTGAAGGGC | TGCTGAAAGT | GGTGCACCCC | GTGACGGGCA | AAGTGCACAC | GATGTTCAAT | 720 |
| CAGGCGTTGA | CGCAAACCGG | GCGCCTCAGC | TCCGTCGAAC | CGAATTTGCA | AAACATTCCG | 780 |
| ATTCGGCTTG | AGGAAGGGCG | GAAAATCCGC | CAGGCGTTCG | TGCCGTCGGA | GCCGGACTGG | 840 |
| CTCATCTTTG | CGGCCGACTA | TTCGCAAATC | GAGCTGCGCG | TCCTCGCCCA | TATCGCGGAA | 900 |
| GATGACAATT | TGATTGAAGC | GTTCCGGCGC | TGGTTGGACA | TCCATACGAA | AACAGCCATG | 960 |
| GACATTTTCC | ATGTGAGCGA | AGAAGACGTG | ACAGCCAACA | TGCGCCGCCA | AGCGAAGGCC | 1020 |
| GTCAATTTTG | GCATCGTGTA | CGGCATTAGT | GATTACGGTC | TGGCGCAAAA | CTTGAACATT | 1080 |
| ACGCGCAAAG | AAGCGGCTGA | ATTTATTGAG | CGATATTTTG | CCAGTTTTCC | AGGTGTAAAG | 1140 |
| CAATATATGG | ACAACATTGT | GCAAGAAGCG | AAACAAAAAG | GGTATGTGAC | GACGCTGCTG | 1200 |
| CATCGGCGCC | GCTATTTGCC | CGATATTACA | AGCCGCAACT | TCAACGTCCG | CACGTTCGCC | 1260 |
| GAGCGGACGG | CGATGAACAC | ACCGATCCAG | GGATCCGCTG | CCGACATCAT | TAAGAAAGCG | 1320 |
| ATGATCGATC | TAAGCGTGAG | CGTGCGCGAA | GAACGGCTGC | AGGCGCGCCT | GTTGCTGCAA | 1380 |
| GGTCATGACG | AACTCATTTT | GGAGGCGCCG | AAAGAGGAAA | TCGACGGCT | GTGCCGCCTC | 1440 |
| GTTCCGGAAG | TGATGGAGCA | AGCCGTGACA | CTTCGCGTGC | CGCTGAAAGT | CGATTACCAT | 1500 |
| TACGGTCCGA | CGTGGTACGA | CGCCAAATAA | AAGCGGCCTG | CCCGCAGCTG | CTCGGTTTTT | 1560 |
| CACGGGGCCG | ACGACAATGA | GCTGTTGCTT | TAAAACAGGT | GCACGAACAG | GAAAAGGAGG | 1620 |
| GAGGC | | | | | | 1625 |

(2) INFORMATION FOR SEQ ID NO:10:

(i) SEQUENCE CHARACTERISTICS:
        (A) LENGTH: 1379 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:10:

```
ATGGCGGCGG CGATTTGGGC GCTTGAAGAG CCGTTGATGG ACGAACTGCG CCGCAACGAA     60

CAAGATCGGC TGCTGACCGA GCTCGAACAC GCGCTGGCTG GCATTTTGGC CAATATGGAA    120

TTTACTGGAG TGAAAGTGGA CACGAAGCGG CTTGAACAGA TGGGGCGGA GCTCACCGAG     180

CAGCTGCAGG CGGTCGAGCG GCGCATTTAC GAACTCGCCG GCCAAGAGTT CAACATTAAC    240

TCGCCGAAAC AGCTCGGGAC GGTTTTATTT GACAAGCTGC AGCTCCCGGT GTTGAAAAAG    300

ACAAAAACCG GCTATTCGAC TTCAGCCGAT GTGCTAGAAA AGCTTGCACC GCACCATGAA    360

ATCGTCGAAC ATATTTTGCA TTACCGCCAA CTCGGCAAGC TGCAGTCAAC GTATATTGAA    420

GGGCTGCTGA AAGTGGTGCA CCCCGTGACG GGCAAAGTGC ACACGATGTT CAATCAGGCG    480

TTGACGCAAA CCGGGCGCCT CAGCTCCGTC GAACCGAATT TGCAAAACAT TCCGATTCGG    540

CTTGAGGAAG GCGGAAAAT CCGCCAGGCG TTCGTGCCGT CGGAGCCGGA CTGGCTCATC     600

TTTGCGGCCG ACTATTCGCA AATCGAGCTG CGCGTCCTCG CCCATATCGC GGAAGATGAC    660

AATTTGATTG AAGCGTTCCG GCGCTGGTTG GACATCCATA CGAAAACAGC CATGGACATT    720

TTCCATGTGA GCGAAGAAGA CGTGACAGCC AACATGCGCC GCCAAGCGAA GGCCGTCAAT    780

TTTGGCATCG TGTACGGCAT TAGTGATTAC GGTCTGGCGC AAAACTTGAA CATTACGCGC    840

AAAGAAGCGG CTGAATTTAT TGAGCGATAT TTTGCCAGTT TTCCAGGTGT AAAGCAATAT    900

ATGGACAACA TTGTGCAAGA AGCGAAACAA AAAGGGTATG TGACGACGCT GCTGCATCGG    960

CGCCGCTATT TGCCCGATAT TACAAGCCGC AACTTCAACG TCCGCACGTT CGCCGAGCGG   1020

ACGGCGATGA ACACACCGAT CCAGGGATCC GCTGCCGACA TCATTAAGAA AGCGATGATC   1080

GATCTAAGCG TGAGCGTGCG CGAAGAACGG CTGCAGGCGC GCCTGTTGCT GCAAGGTCAT   1140

GACGAACTCA TTTTGGAGGC GCCGAAAGAG GAAATCGGAC GGCTGTGCCG CCTCGTTCCG   1200

GAAGTGATGG AGCAAGCCGT GACACTTCGC GTGCCGCTGA AAGTCGATTA CCATTACGGT   1260

CCGACGTGGT ACGACGCCAA ATAAAAGCGG CCTGCCCGCA GCTGCTCGGT TTTTCACGGG   1320

GCCGACGACA ATGAGCTGTT GCTTTAAAAC AGGTGCACGA ACAGGAAAAG GAGGGAGGC   1379
```

(2) INFORMATION FOR SEQ ID NO:11:

(i) SEQUENCE CHARACTERISTICS:
        (A) LENGTH: 1142 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:11:

```
ATGGCGCCAA ACAGCTCGG GACGGTTTTA TTTGACAAGC TGCAGCTCCC GGTGTTGAAA      60

AAGACAAAAA CCGGCTATTC GACTTCAGCC GATGTGCTAG AAAAGCTTGC ACCGCACCAT    120

GAAATCGTCG AACATATTTT GCATTACCGC CAACTCGGCA AGCTGCAGTC AACGTATATT    180

GAAGGGCTGC TGAAAGTGGT GCACCCCGTG ACGGGCAAAG TGCACACGAT GTTCAATCAG    240
```

```
GCGTTGACGC AAACCGGGCG CCTCAGCTCC GTCGAACCGA ATTTGCAAAA CATTCCGATT      300

CGGCTTGAGG AAGGGCGGAA AATCCGCCAG GCGTTCGTGC CGTCGGAGCC GGACTGGCTC      360

ATCTTTGCGG CCGACTATTC GCAAATCGAG CTGCGCGTCC TCGCCCATAT CGCGGAAGAT      420

GACAATTTGA TTGAAGCGTT CCGGCGCTGG TTGGACATCC ATACGAAAAC AGCCATGGAC      480

ATTTTCCATG TGAGCGAAGA AGACGTGACA GCCAACATGC GCCGCCAAGC GAAGGCCGTC      540

AATTTTGGCA TCGTGTACGG CATTAGTGAT TACGGTCTGG CGCAAAACTT GAACATTACG      600

CGCAAAGAAG CGGCTGAATT TATTGAGCGA TATTTTGCCA GTTTTCCAGG TGTAAAGCAA      660

TATATGGACA ACATTGTGCA AGAAGCGAAA CAAAAAGGGT ATGTGACGAC GCTGCTGCAT      720

CGGCGCCGCT ATTTGCCCGA TATTACAAGC CGCAACTTCA ACGTCCGCAC GTTCGCCGAG      780

CGGACGGCGA TGAACACACC GATCCAGGGA TCCGCTGCCG ACATCATTAA GAAAGCGATG      840

ATCGATCTAA GCGTGAGCGT GCGCGAAGAA CGGCTGCAGG CGCGCCTGTT GCTGCAAGGT      900

CATGACGAAC TCATTTTGGA GGCGCCGAAA GAGGAAATCG GACGGCTGTG CCGCCTCGTT      960

CCGGAAGTGA TGGAGCAAGC CGTGACACTT CGCGTGCCGC TGAAAGTCGA TTACCATTAC     1020

GGTCCGACGT GGTACGACGC CAAATAAAAG CGGCCTGCCC GCAGCTGCTC GGTTTTTCAC     1080

GGGGCCGACG ACAATGAGCT GTTGCTTTAA AACAGGTGCA CGAACAGGAA AAGGAGGGAG     1140

GC                                                                    1142
```

(2) INFORMATION FOR SEQ ID NO:12:

(i) SEQUENCE CHARACTERISTICS:
        (A) LENGTH: 890 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:12:

```
ATGGGCCGCC TCAGCTCCGT CGAACCGAAT TTGCAAAACA TTCCGATTCG GCTTGAGGAA       60

GGGCGGAAAA TCCGCCAGGC GTTCGTGCCG TCGGAGCCGG ACTGGCTCAT CTTTGCGGCC      120

GACTATTCGC AAATCGAGCT GCGCGTCCTC GCCCATATCG CGGAAGATGA CAATTTGATT      180

GAAGCGTTCC GGCGCTGGTT GGACATCCAT ACGAAAACAG CCATGGACAT TTTCCATGTG      240

AGCGAAGAAG ACGTGACAGC CAACATGCGC CGCCAAGCGA AGGCCGTCAA TTTTGGCATC      300

GTGTACGGCA TTAGTGATTA CGGTCTGGCG CAAAACTTGA ACATTACGCG CAAAGAAGCG      360

GCTGAATTTA TTGAGCGATA TTTTGCCAGT TTTCCAGGTG TAAAGCAATA TATGGACAAC      420

ATTGTGCAAG AAGCGAAACA AAAGGGTAT GTGACGACGC TGCTGCATCG GCGCCGCTAT      480

TTGCCCGATA TTACAAGCCG CAACTTCAAC GTCCGCACGT TCGCCGAGCG GACGGCGATG      540

AACACACCGA TCCAGGGATC CGCTGCCGAC ATCATTAAGA AAGCGATGAT CGATCTAAGC      600

GTGAGCGTGC GCGAAGAACG GCTGCAGGCG CGCCTGTTGC TGCAAGGTCA TGACGAACTC      660

ATTTTGGAGG CGCCGAAAGA GGAAATCGGA CGGCTGTGCC GCCTCGTTCC GGAAGTGATG      720

GAGCAAGCCG TGACACTTCG CGTGCCGCTG AAAGTCGATT ACCATTACGG TCCGACGTGG      780

TACGACGCCA AATAAAAGCG GCCTGCCCGC AGCTGCTCGG TTTTCACGG GGCCGACGAC      840

AATGAGCTGT TGCTTTAAAA CAGGTGCACG AACAGGAAAA GGAGGGAGGC                 890
```

(2) INFORMATION FOR SEQ ID NO:13:

(i) SEQUENCE CHARACTERISTICS:

```
        (A) LENGTH: 28 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:13:

CATGCCATGG TTGATTCAAA GCGGGCGG                                              28

(2) INFORMATION FOR SEQ ID NO:14:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:14:

CATGCCATGG CGGCGATTTG G                                                     21

(2) INFORMATION FOR SEQ ID NO:15:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:15:

CATGCCATGG CGCCAAAACA GCTCGGG                                               27

(2) INFORMATION FOR SEQ ID NO:16:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:16:

CATGCCATGG GCGCGCTCAG CTC                                                   23

(2) INFORMATION FOR SEQ ID NO:17:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:17:

CATGCCATGG CCGTCCAA                                                         18
```